(12) United States Patent
Riess et al.

(10) Patent No.: US 8,763,478 B2
(45) Date of Patent: Jul. 1, 2014

(54) ENVIRONMENTAL SAMPLER AND METHODS OF USING SAME

(75) Inventors: Mark James Riess, Walla Walla, WA (US); Lori Dawn Crass, Kennewick, WA (US)

(73) Assignee: Unibest International, LLC, Walla Walla, WA (US)

( * ) Notice: Subject to any disclaimer, the term of this patent is extended or adjusted under 35 U.S.C. 154(b) by 113 days.

(21) Appl. No.: 13/227,445

(22) Filed: Sep. 7, 2011

(65) Prior Publication Data

US 2012/0222500 A1    Sep. 6, 2012

Related U.S. Application Data

(60) Provisional application No. 61/380,320, filed on Sep. 7, 2010.

(51) Int. Cl.
*G01N 1/12* (2006.01)

(52) U.S. Cl.
USPC ...................................................... 73/863.21

(58) Field of Classification Search
None
See application file for complete search history.

(56) References Cited

U.S. PATENT DOCUMENTS

| | | | |
|---|---|---|---|
| 4,976,866 A * | 12/1990 | Grinstead et al. | 210/638 |
| 5,149,436 A * | 9/1992 | Taniguchi et al. | 210/657 |
| 5,322,388 A | 6/1994 | Wells | |
| 5,355,736 A | 10/1994 | Skogley | |
| 6,112,602 A | 9/2000 | Mitra | |
| 6,401,547 B1 | 6/2002 | Hatfield et al. | |
| 7,325,443 B2 | 2/2008 | De Jonge et al. | |
| 7,399,447 B2 | 7/2008 | Bowers et al. | |
| 2008/0105064 A1 | 5/2008 | Halland | |
| 2009/0007704 A1 | 1/2009 | Bowers et al. | |
| 2009/0084976 A1 | 4/2009 | Camilli | |
| 2010/0031759 A1 | 2/2010 | Tovena-Pecault | |

* cited by examiner

*Primary Examiner* — Robert R Raevis

(74) *Attorney, Agent, or Firm* — Pedersen and Company, PLLC; Ken J. Pedersen; Barbara S. Pedersen

(57) ABSTRACT

An environmental testing and monitoring system uses a sampler to hold resin or other adsorbent for contaminants and pollutants uptake from water or air, and preferably includes remote real-time sensors that detect and transmit physical and/or chemical data by wireless or wired telemetry and GPS systems. The sampler and sensors may be attached to a fixed or floating buoy system that is capable of solar charging or may be affixed to other supports to allow precise placement in, and easy retrieval from, various structures and environments including fresh and saltwater, soil and sediment, water and sludge pipes and vessels, air, and gaseous streams and emissions. Time-measured, mass-balanced data sets may be achieved from the extended-time-accumulated values from the resin/adsorbent sampler left in place for an extended time, and preferably from the real-time sensors that transmit a steady stream of information throughout said extended time.

13 Claims, 11 Drawing Sheets

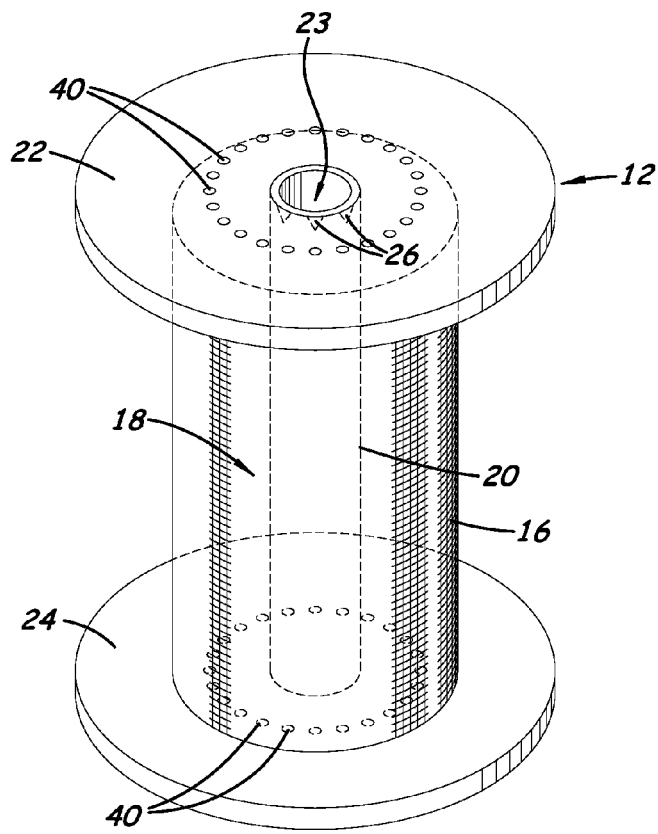
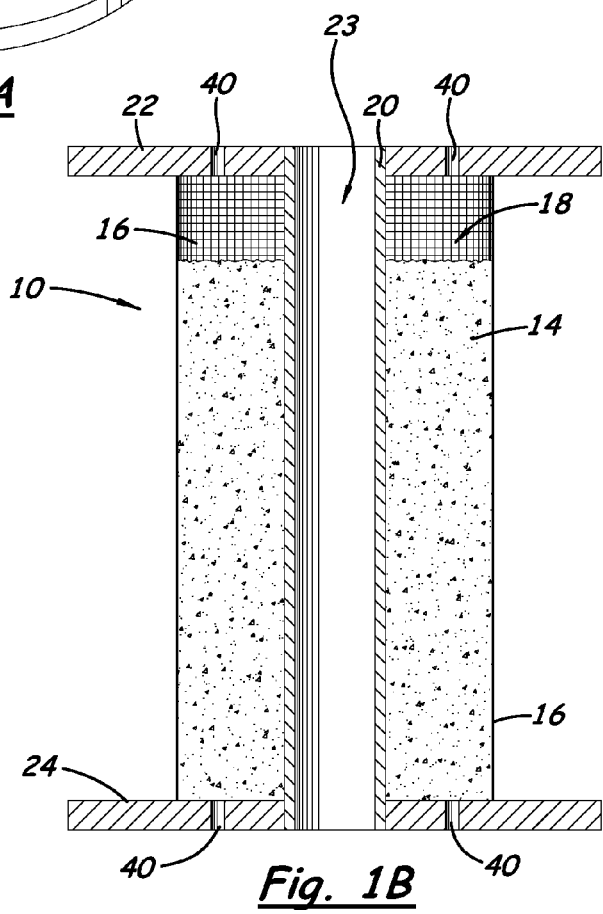

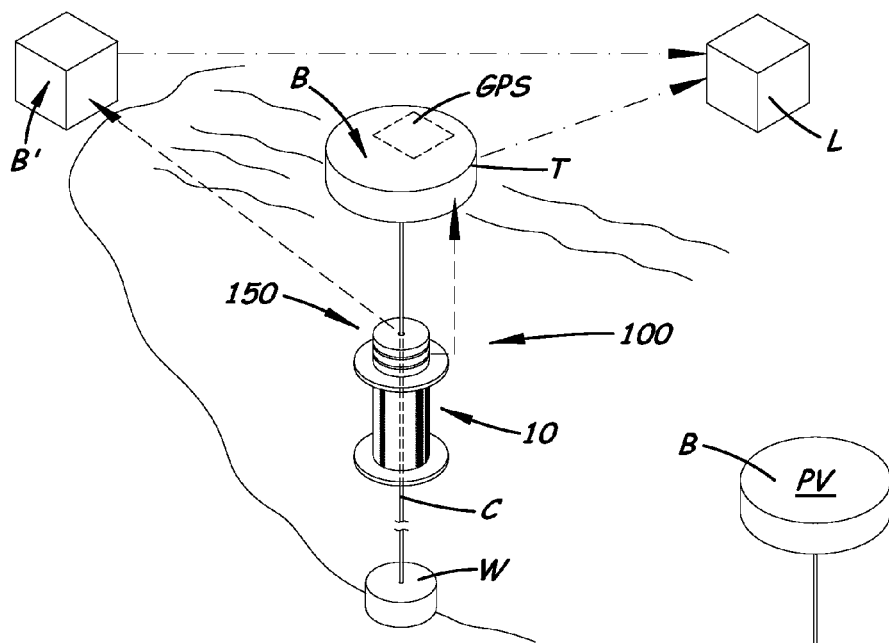
*Fig. 4*
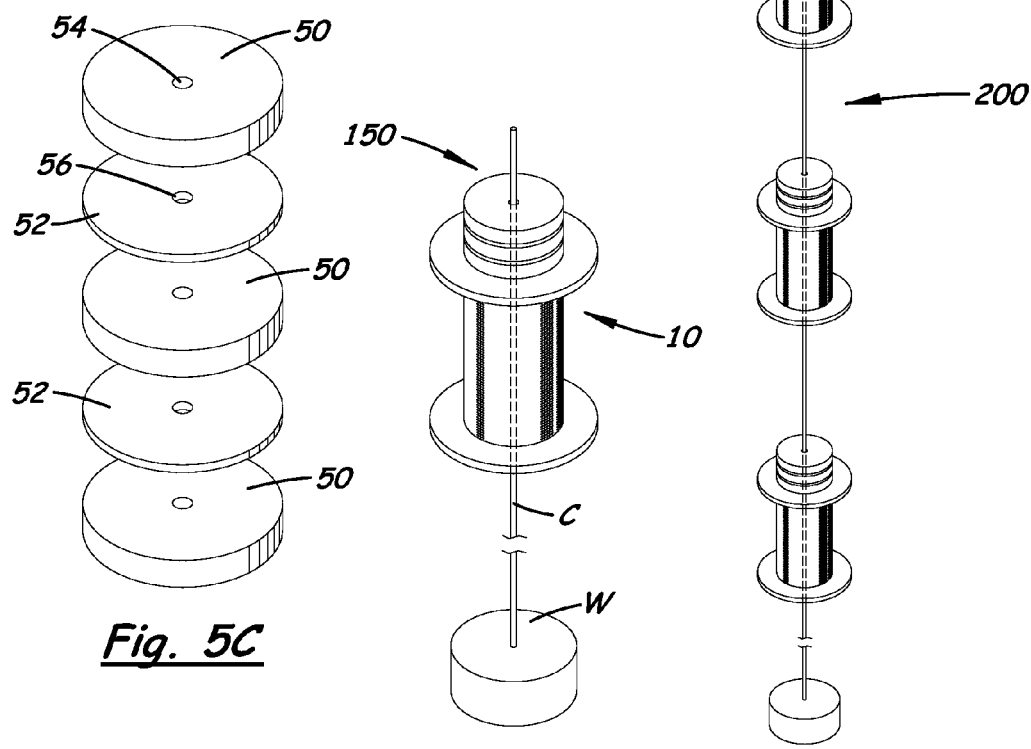
*Fig. 5C*   *Fig. 5B*   *Fig. 5A*

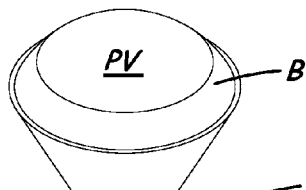
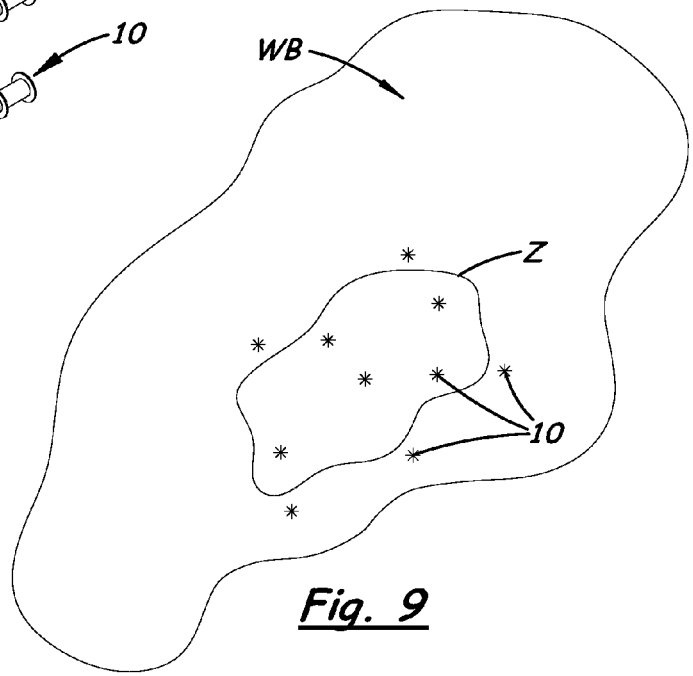
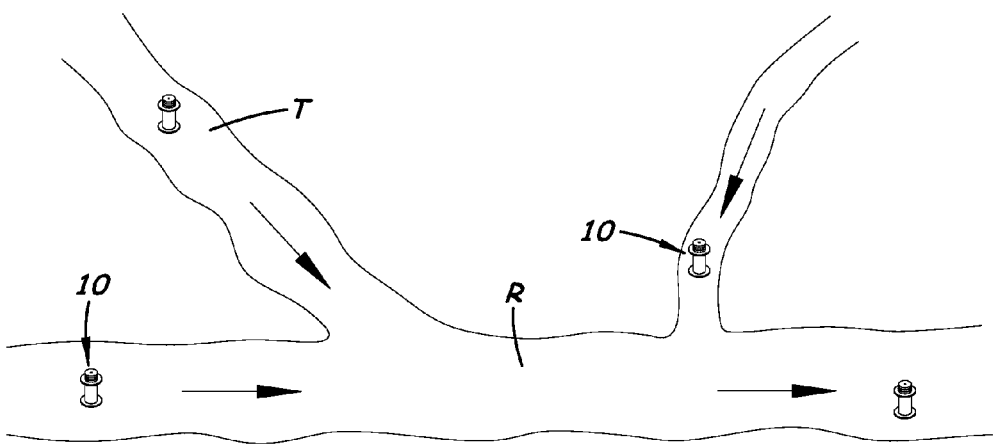
Fig. 7
Fig. 9
Fig. 8

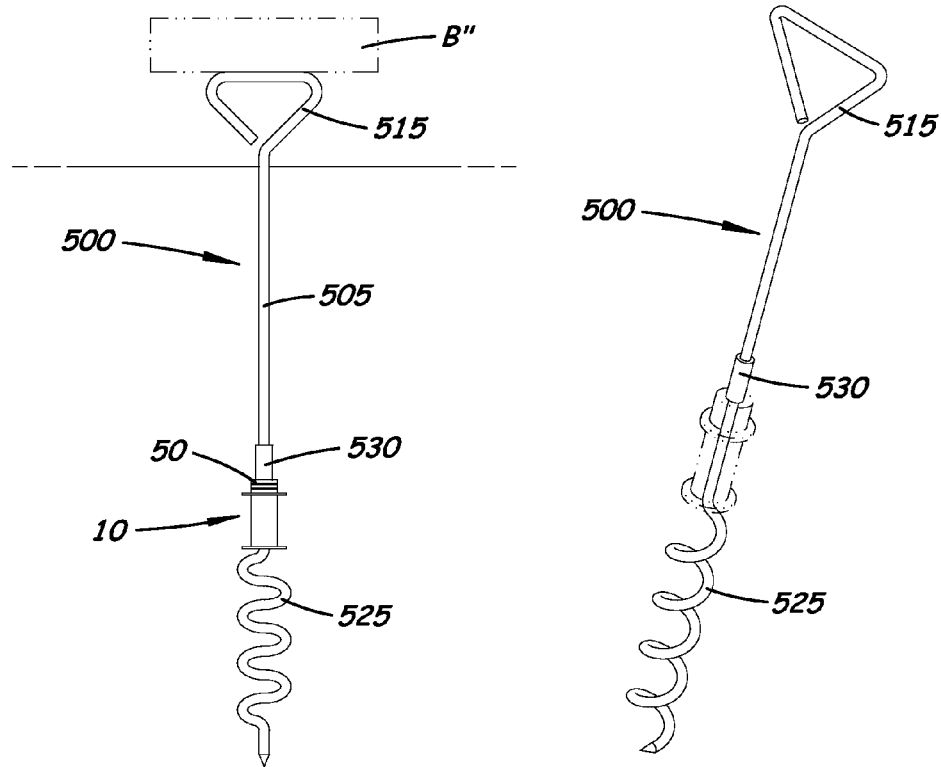
Fig. 10A   Fig. 10B
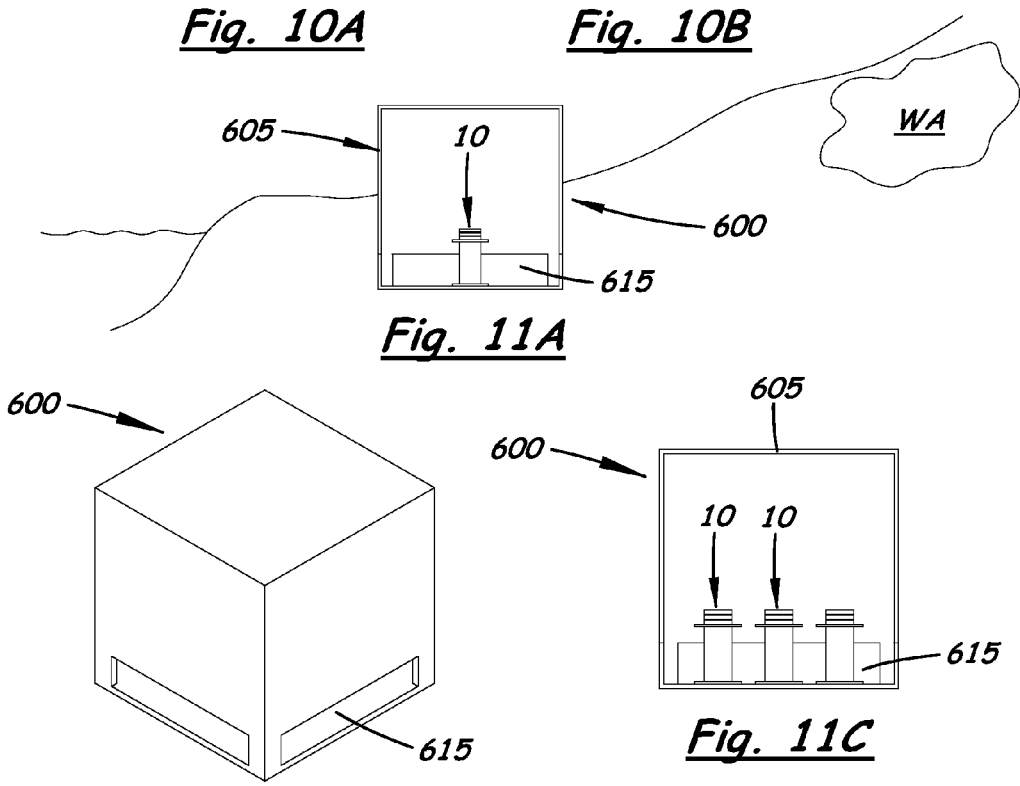
Fig. 11A
Fig. 11B   Fig. 11C

ENVIRONMENTAL SAMPLER AND METHODS OF USING SAME

This application claims priority of Provisional Application Ser. No. 61/380,320, filed Sep. 7, 2010, and entitled "Environmental Sampler", which is incorporated herein by this reference.

FIELD OF THE INVENTION

This invention relates generally to ecological monitoring and methods for locating and tracking contaminants that may affect human health and the environment. More specifically, this invention relates to deploying apparatus in aqueous, groundwater, sediment, soil, and atmospheric environments, and measuring site-specific contaminants. Embodiments of the invention may include using the apparatus to identify point source locations, distribution of contaminants, contaminant concentrations, residues, and chemical build-up and release models. Another beneficial use can include the identification, measurement, tracking, and assessment of contaminants associated with Natural Resource Damage Assessments such as the measuring of petroleum and petroleum by-products associated with a large crude oil or other release or spill.

SUMMARY OF THE INVENTION

The present invention comprises an apparatus and/or methods for detecting and/or monitoring environmental pollutants and/or chemicals, such as, but not limited to, nutrient loading, herbicide/pesticides, heavy metals, organic compounds, radionuclides, illegal-drugs or drug-related by-products, and/or chemicals and chemical by-products important to national security and natural resource damage assessments. According to certain embodiments of the invention, a sampler system comprises ion-exchange resin(s) and/or other adsorbent(s) and is placed in any environmental medium in which fluid from the environmental medium may contact the resin/adsorbent. The sampler may be placed in aqueous environments such as rivers, lakes, or streams, in soil or sediment, on or in ground where water-run-off flows or seeps, in sewers or other waste streams or containment systems, and/or in air or other gaseous environments. Samplers are placed at strategic locations, to collect contaminants to establish baseline concentrations, determine location(s) of contaminant source(s), establish contaminant migration and distribution routes, and/or determine contaminant concentrations at various distances from the source. Samplers are collected after a predetermined time period, and then analyzed using laboratory protocols and methods appropriate for the particular ion exchange resin(s)/adsorbent(s) of the sampler(s). Certain embodiments comprise samplers placed in and/or downstream of chimneys/discharge stacks to monitor airborne contaminants. In other embodiments, samplers are placed in discharge piping, such as sewer piping, to monitor for NPDES, POTW, and chemical/chemical by-products associated with illegal drug manufacturing or materials important to national security.

A preferred embodiment of the sampler system comprises a sampler enclosure that houses resin(s) and/or other adsorbent(s), with one or more real-time sensors provided closely adjacent to the sampler to sense physical conditions, elements, or other characteristics of the media surrounding the sampler. One or more samplers with real-time sensors may be held in place by various supports, for example, a cable, a buoy, a rigid arm, a motorized bar/bracket, a spike, or screw-in stake.

The preferred sampler includes an enclosure comprising a generally cylindrical, outer screen, which may include screen, mesh, perforated, or other fluid-permeable material that allows fluids including water or air, and contaminants carried therein, through the screen to reach ion-exchange resin or other adsorbent in a space inside the enclosure. The enclosure may include a platform and a cap at opposite ends of the screen, and a post extending through the sampler at or near the central axis of the sampler. The post may he adapted to connect the platform and cap together, with the screen between said platform and cap, and with the annular space between the post and the screen receiving resin/adsorbent. The post may be hollow, or otherwise adapted to receive or connect to a cable, such as a wire, string, chain, or other elongated member, for suspending of the sampler in a desired location. The side wall of the post may be solid-walled, that is, continuous and without perforations. Alternatively, the side wall of the post may be, or have portions that are, non-continuous, including screen, mesh, perforated material, or other fluid-permeable material. In such cases, the post would preferably be hollow so that fluid could flow into the hollow post and into and out the non-continuous post side wall to reach the resin/adsorbent.

"Fluid-permeable" means in this context that the fluid may pass through the material with little or no filtering of the contaminants of interest. The screen and post mesh size may be selected, however, to be a filter or barrier to larger items such as gravel, sticks, or leaves.

The enclosure may be taken at least partially apart for insertion of resin or other adsorbent, including loose resin/adsorbent or fluid-permeable packet(s)/container(s) of resin/adsorbent. The enclosure and/or entire sampler may be retrieved from the environment for transport to a laboratory for analysis of the resin/adsorbent. Or, the enclosure may be taken at least partially apart on-site for a quick change-out of the resin/adsorbent and re-installation of the sampler in the environment, in which case only the resin/adsorbent needs to be taken to the laboratory. In the later case, environmental monitoring may continue, with a fresh resin/adsorbent, after only an extremely short interruption.

An optional, but preferred, adaptation for the sampler system is to provide a resin/adsorbent sampler plus one or more real-time sensors outside of, but preferably connected or otherwise closely-associated with, the resin/adsorbent sampler. Options for said real-time devices include one or more discs, membranes, packets, or other forms sensor material that react to physical parameters and environmental contaminants, for example, temperature, dissolved oxygen and other elements, pH, but not limited to, clarity, bacteria, conductivity, organic compounds, and/or inorganic compounds. The real-time sensors may be membrane, solid, or electrical/mechanical sensors, for example, that are provided above, below, or beside the resin/adsorbent sampler, with the preferred configuration being one or more sensors being coaxial with the post of the sampler and connected to the sampler by the cable that suspends the sampler or by other means. In certain embodiments, multiple sensors are on the cable and stacked above the sampler.

Remote telemetry may be provided that is in communication with said real-time sensors, to provide real-time measurement of physical parameters and environmental contaminants. Telemetry may be integrated with a network of multiple samplers, on the same support structure or various support structures, to provide measurements over a large geographical area. Real-time sensors are currently optional, but may become more and more important elements of the apparatus and process, as new and more accurate sensors for contaminants and physical parameters are developed by those of skill in sensor art.

The preferred embodiments of real-time sensors are those that are symmetrical around a central axis, and which may be installed at or near the resin/adsorbent sampler, for example coaxial with the post of the sampler. Symmetrical real-time sensors include, for example, circular plates, spheres, cylinders, and oblate-shapes. The especially-preferred symmetrical real-time sensor is called a "sensor disc" hereafter, and is a generally-plate-shaped or generally-wafer-shaped device that is generally or exactly symmetrical around its central axis and provided closely-adjacent to a sampler. Such a shape is expected to give excellent and consistent data, via wireless or less-preferably wired means, as discussed in more detail later in this document. Non-symmetrical sensors, for example bars or cubes, may be used if they are affixed to account for directional influences such as flow or air patterns.

The real-time sensors may be "strung" on the cable, bar, or other support system that holds or suspends the sampler(s), preferably immediately adjacent the sampler. The sensors that are "strung" coaxially on a cable with the sampler may rest by gravity on top of the sampler, or be connected above or below the sampler by a clip, bracket, tether or other preferably-detachable fastener. Or, the sensors may be connected to a side of the sampler, but this is less preferred due to the asymmetry inherent in most versions of such an arrangement.

The preferred coaxial, or otherwise closely-adjacent or very near placement, of sensors relative to the samplers, allows for "immediately adjacent" comparisons of the data from the sensors and also the data (lab analysis) of the sampler. Preferably, each real-time sensor is within less than 6 inches of its respective sampler, and more preferably within less than 3 inches of its respective sampler. This allows comparison and correlation of both data sets from a single apparatus system, that is, resin/adsorbent data plus real-time data from a single combined unit of resin sampler plus sensor(s).

Certain embodiments of the invention may provide a means for monitoring environmental pollutants and other contaminants to support short-term, rapid environmental assessments, long-term monitoring of catastrophic environmental events, and/or natural resource damage assessments. Certain embodiments of the invention may provide means to monitor and manage treatment and application of herbicides and pesticides in aquatic environments. Certain embodiments of the invention may provide means to screen for chemicals (including hazardous wastes), chemical by-products, and radionuclides. Certain embodiments of the invention may help minimize the potential for environmental damage and exposure to the public. Furthermore, certain embodiments of the invention utilize commercially-available resins/adsorbents, sensing materials, and telemetry components, and also known laboratory analysis methods for said resins/adsorbents. The preferred embodiments of the invention rely on relatively few items of support equipment and the application and methods associated with the preferred embodiments can be completed in a very short amount of time compared to conventional environmental monitoring processes.

BRIEF DESCRIPTION OF THE DRAWINGS

FIG. 1A is a perspective view of one embodiment of the invented resin/adsorbent sampler, without any resin or adsorbent in the sampler, wherein this sampler comprises a hollow central post that has a solid and continuous side wall so that it is not fluid-permeable.

FIG. 1B is an axial-cross-sectional view of the sampler of FIG. 1A, which shows an embodiment of granular resin inside the sampler.

FIGS. 1A and B and 2A and B show an embodiment of the outer screen of the sampler that is substantially or entirely mesh material. In FIGS. 1A and 2A, however, only small portions of the screen are drawn with square-mesh markings, so that the other portions of the sampler may be easily seen in the Figure.

FIG. 4 shows a sampler system according to one embodiment of the invention installed in a body of water, such as a lake, a waterway such as a stream or river, or the ocean.

FIG. 5A portrays an embodiment of the sampler system wherein multiple samplers are "strung" on a single cable, with multiple real-time sensor discs associated with each sampler by being "strung" on the same cable above the associated sampler.

FIG. 5B is an enlarged detail view of the lower portion of the embodiment of FIG. 5A.

FIG. 5C is an exploded view of the three sensor discs and two spacers of FIG. 5B, wherein the spacers are for cushioning and protection from friction and wear and/or for electronic/electric insulation and/or static prevention.

FIG. 7 is a perspective view of another embodiment wherein a main cable is held between a weight and a buoy that preferably comprises telemetry equipment, and transverse tethers extend from part-way along the cable to tether two samplers with sensor discs to the main cable. in a configuration that allows the samplers and discs to float generally horizontally out from the main cable. This way, the current in a waterway will send each sampler and its discs downstream a distance generally equal to the length of its tether. FIG. 7 shows the two tethers to be about equal, but tethers of different lengths may be beneficial to test/monitor water at different distances from the single buoy and weight assembly.

FIG. 8 schematically depicts one embodiment of the invention wherein multiple samplers are placed in rivers and tributary streams for watershed management. Samplers may be fixed or weighted-down to the river/tributary bottom and suspended at selected depths to establish baseline conditions and also to indicate pollutant/contaminant point source location. Sampler systems each with a single sampler may be used, or multiple-sampler systems may be used, for example, such as shown in FIG. 4, 6A-C, or 7.

FIG. 9 depicts another embodiment of the invention wherein samplers, each indicated with an asterisk, are distributed within a lake to obtain environmental measurements, for example to manage application of herbicides/pesticides to control noxious weeds within a particular portion of the lake.

FIGS. 10A and B are a side view and a perspective view of a stake embodiment for insertion into dirt, sediment, shoreland, wetlands or other ground, soil, or other generally solid location.

FIGS. 11A and C are cross-sectional side views of an alternative embodiment of the invented sampler system wherein one (11A) or more (11C) samplers are provided in a container rather than on a cable or tether, for example, to receive and monitor water run-off down a hill or shore. FIG. 11B is a perspective view of the container of FIGS. 11A and C.

Figure 2A:
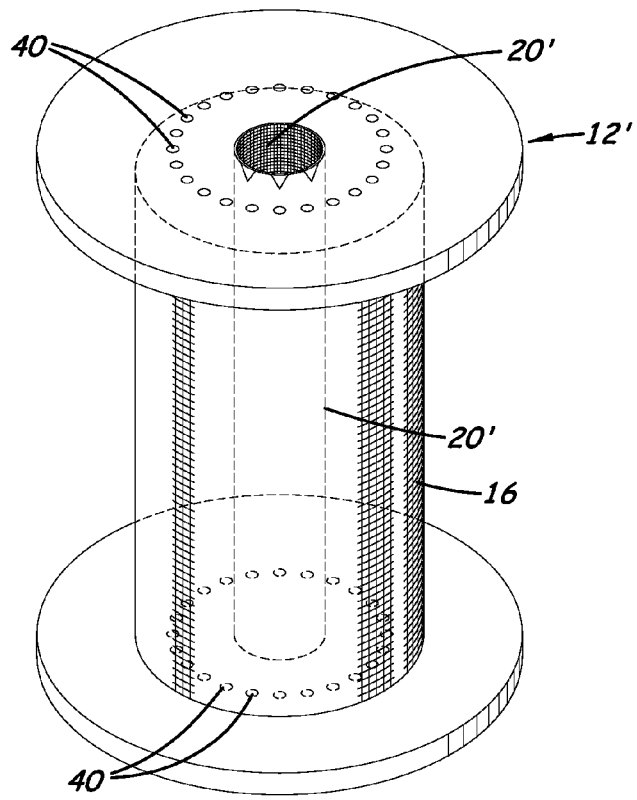
FIG. 2A is a perspective view of an alternative embodiment of the invented resin/adsorbent sampler, without any resin or adsorbent in the sampler, wherein this sampler comprises a hollow central post that is made of screen/mesh so that it is fluid-permeable.

It should be noted that many embodiments of the invented samplers and real-time sensors are enlarged in the figures relative to the environment and environmental equipment in the figures, for clarity. Many samplers and sensors will be smaller than implied by the figures.

DETAILED DESCRIPTION OF PREFERRED EMBODIMENTS OF THE INVENTION

Referring to the figures, there are shown several but not the only, embodiments of the invented sampler system and methods of using said sampler system. The sampler system may be used to monitor various locations and media in the environment, for example, to monitor water or air for various containments and chemicals. As best portrayed in FIGS. 1A and B, 2A and B, and 3A and B, the sampler system uses a sampler 10 comprising a housing 12 adapted to contain one or more resins and/or adsorbents 14, wherein the housing 12 comprises a side-wall that is entirely or substantially fluid-permeable to allow water and air to flow to the resin/adsorbent 14 inside the housing.

Therefore, the term "adsorbent" hereafter and in the claims is defined as any material that adsorbs, wherein adsorbs or adsorption may be defined as the adhesion of atoms, ions, biomolecules or molecules of gas, liquid, or dissolved solids to a surface. This process creates a film of the adsorbate (the atoms, ions, or molecules being accumulated) on the surface of the adsorbent. Adsorption is therefore a surface phenomenon, and so can be used to take up said adsorbate and then to release or substantially release the adsorbate for laboratory analysis by known processes such as contact by a leaching liquid.

Samplers and preferably real-time sensors may be provided singly or in groups, and may be installed in the environmental medium, or in a location where they will at least intermittently contact the environmental medium (for example, with tides, increased flow in a sewer, or other changes in the medium). Installation may comprise attachment to or containment in a box or other container that has apertures so that the medium will reach the sampler/sensors. Or, installation may be on a flexible elongate member such as cable (including strings, cords, chains), on a rigid or generally rigid elongated member (such as a bar, board, post, hanger), and/or hanging down on a flexible, rigid, or generally rigid member from a support base. Support bases may comprise, for example, a buoy including any floating object, or a fixed or usually-fixed member such as a manhole cover, upstanding pipe, pier, bridge, tree, smokestack, or other infrastructure or building portion. Support bases may include telemetry and/or GPS in some embodiments. The term "telemetry base" is also used herein, and refers to apparatus that is distanced from the sampler and real-time sensor, for example, to receive signals transmitted from the real-time sensors. A telemetry base is not necessarily physically connected to, supporting, or holding the sampler and real-time sensor, but is associated with the sampler system at least by operative connection through telemetry signals. A telemetry base, however, may also in certain embodiments be the support base, for example, a buoy that comprises telemetry apparatus and preferably also GPS apparatus, wherein the sampler and/or the real-time sensor are connected to and typically suspended from the buoy.

The fluid-permeable side-wall is preferably a cylindrical screen 16, and an annular space 18 exists between the screen and a center post 20 of the sampler. The center post 20 preferably is hollow so that it comprises a longitudinal passageway 23 through which a cable, bar, or other elongated member may be passed or otherwise connected to the sampler. This way, the sampler may be hung in water, air or other liquid or gasses, and multiple samplers may be "strung" on a single cable/member, as will be further discussed below. The sampler(s) and disc(s) may be fastened to the cable/member (including a rod, bar, arm or other member) by various fasteners, including ties, knots, clips, frictional members, grippers, screws, nuts, spacers, brackets, or enlarged-diameter cable connectors, for example. Ranges, nuts, or other structure that is of larger diameter than the post passageway 23, may be fixed/integral with the cable below and preferably also above each sampler-disc assembly, to prevent the sampler-disc assembly from sliding downward or upward on the cable. Or, fasteners may be provide inside the hollow passageway 23 that grip or attach to the sampler, to prevent the samplers from sliding along the cable/member until the fastener is unfastened or unlatched. Specific fasteners are not drawn in the figures, as various ways and fasteners will be apparent to those of skill for fixing the sampler to the cable/member, supporting the sampler on the cable/member, or otherwise prevent sliding of the sampler along the cable/member.

The housing 12 further comprises a cap 22 and a platform 24 at opposite ends of the screen 16, which are connected and retained together by the post 20. The post 20 may be molded integrally with, or otherwise fixed to, the platform 24, or, less preferably, may be detachable from the platform, for example, by a threaded connection or other fastening device. The cap 22 preferably detaches from the post 20, for opening up the sampler 10 and its annular space 18. Snap-fit tabs 26 or other fasteners may be provided on an end of the post 20 and/or on the cap 22, for fastening the cap to the post. The cap is fastened to the post in a position that presses the screen 16 tightly between the cap and platform, so that resin/adsorbent will not leak out form the sampler. The screen may be fixed permanently to the platform, with the cap preferably having a circular indent or seal in its underside for sealing engagement with the screen. Or, both platform and cap may have a circular indent or seal for sealing engagement with the screen. By "sealing engagement" in this context, it is meant sufficient firm contact to prevent the screen from falling/moving away from the cap or platform and opening a hole that would allow resin, adsorbent, or resin/adsorbent packets from falling out of the sampler. "Sealing" in this context does not mean a fluid-seal, as it acceptable for fluid to flow throughout the sampler.

FIGS. 1 A and B portray a sampler 10 that has a solid-walled post 20, and loose, granular ion-exchange resin in its annular space 18. This post 20 will not let fluid through its side-wall, but fluid may enter the sampler from all the way around the circumference of the screen 16. FIGS. 2A and B portray a sampler 10' that has a housing 12' with fluid-permeable post 20', for example, a post made of the same or similar screen as outer screen 16. This post allows fluid flowing into the hollow passageway of the post 20' to enter the annular space from the inside of the sampler to contact the resin/adsorbent.

Figure 3A:
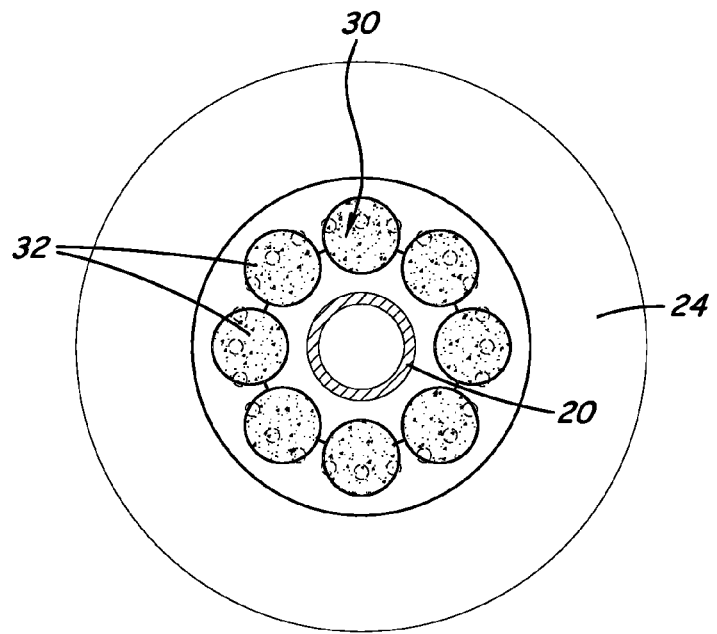
FIG. 3A is a top view of a sampler as in FIGS. 1A and 1B, with the cap removed to show a multiple-compartment packet of resin/adsorbent provided, in the annular space of the sampler, instead of loose resin/adsorbent.

FIGS. 3A and B portray a sampler 10" containing a multiple-compartment packet 30 of resin, for example, fluid-permeable fabric sewn to have multiple compartments 32 each containing resin(s). A packet-style container, especially one that includes multiple compartments, tends to keep the resin distributed more evenly in the annular space and all around the circumference of the sampler. The compartments 32 extend axially all or substantially all the length of the packet, so that "vertical columns" of resin are provided in the space 18, in effect, evenly spaced around the circumference of the sampler. In the following figures, samplers that look like FIG. 1A are shown in various environments, and it will be understood that the samplers have loose and/or packets of resin/adsorbent, and it will be understood that samplers such as those in FIGS. 1A and B, 2A and B, 3A and B, or other embodiments within the broad scope of the invention, may be used in the various environments.

Figure 2B:
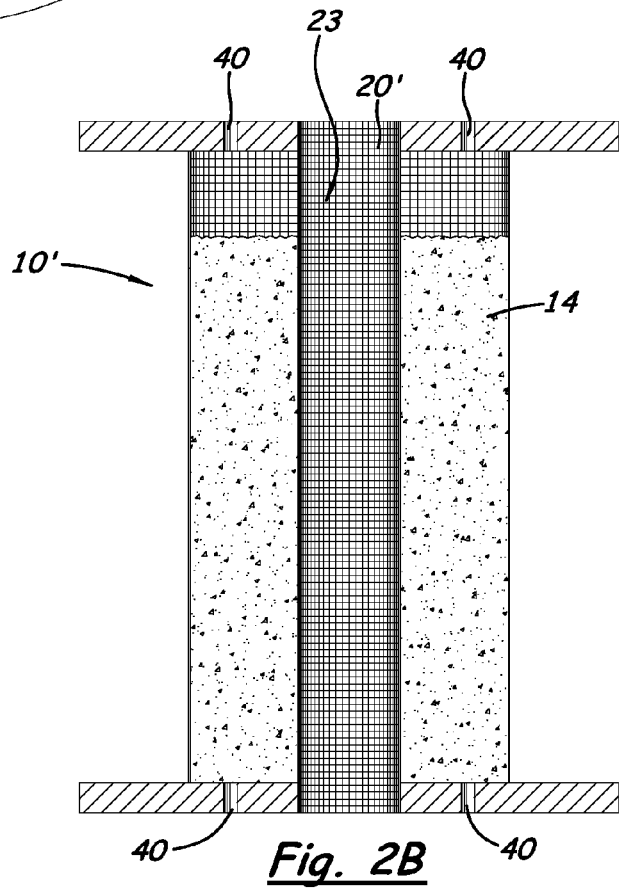
FIG. 2B is an axial-cross-sectional view of the sampler of FIG. 2A, which shows an embodiment of granular resin inside the sampler.
Figure 3B:
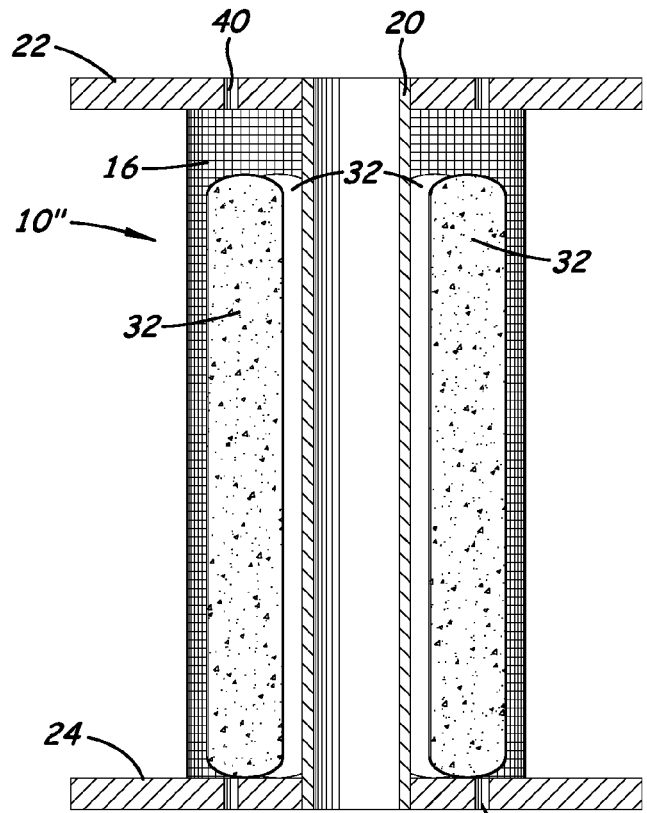
FIG. 3B is an axial-cross-sectional view of the sampler of FIG. 3A (with the cap installed, showing two of the compartments of the packet in cross-section, at the right and left of the central post of the sampler.

FIGS. 1-3 show apertures 40 in the cap 22 and platform 24, for allowing solvent or other fluid to enter or leave the annular space 18 from the top and bottom of the sampler. This is particularly useful in laboratory testing as will be discussed in more detail below referring to FIGS. 17 and 18. The apertures 40 are arranged in a circular pattern in each of the cap and platform, as this will tend to provide evenly distributed flow, during laboratory analysis, into the annular space for even and generally predictable contact of solvents or other chemical with the resin/adsorbent.

As shown to best advantage by the sampler system 100 and details in FIGS. 4 and 5A-C, one or more optional real-time sensors, for example the preferred sensor discs 50 may be included in the sampler system to sense physical conditions, elements, or chemicals in real-time at or near the sampler. A cable C holding at least one sampler 10 extends down from the buoy. An assembly 150 of sensor discs 50 and spacers 52 are strung on the cable C as well, directly and closely above the sampler 10, and a weight W or other anchor point on or near the lake, stream, or ocean sediment/soil-bed is provided to keep the sampler system generally vertical in the water at a fixed or substantially fixed location in the water. The dashed communication lines in FIG. 4 schematically portray how the real-time sensors comprise electronics and transmission systems to send wireless signals (one or more separate signals), comprising sensed data, to a telemetry base, which may be the buoy B and/or optionally a shore-base B' on the shore. The buoy B and/or the shore-base B' comprise(s) telemetry equipment preferably with GPS that transmits the data on to a distant lab or research station (dash-and-dot lines) for recording and analysis. Wireless or less-preferably wire telemetry T, preferably combined with a GPS system, is preferably provided to allow data transfer from the real-time sensor discs 50 to a remote recorder, a lab or research station, or other computer and/or control station (L), that is typically distant from the system 100, for example, miles away. This way, the real-time data may be combined/integrated with the resin/adsorbent lab data to provide a more complete and accurate view of the environment being monitored, including over large geographical areas and with GPS positioning data describing the location of the sampler systems. While all the details of telemetry and GPS apparatus for embodiments of the invention are not listed or drawn herein, said telemetry and GPS apparatus will be understood by one of skill in these arts and conventional telemetry and GPS apparatus can be obtained commercially and implemented without undue experimentation.

FIG. 5A portrays an embodiment of the sampler system 200 wherein multiple samplers are "strung" on a single cable, with multiple real-time sensor discs associated with each sampler by being "strung" on the same cable above the associated sampler. As described for FIG. 4, the real-time sensor discs 50 may communicate, preferably wirelessly, with a telemetry and/or GPS base, for further transmission to the lab or research station. The embodiments shown in FIGS. 4 and 5A preferably include solar-power capability and/or batteries, for example, a photovoltaic panel PV on the top of the buoy B to power the telemetry/GPS.

FIG. 5B is an enlarged detail view of the lower portion of the embodiment of FIG. 5A. FIG. 5B shows one sampler, three sensor discs 50 (with spacers 52 between them) above the sampler, and a weight below the sampler, all being provided on the single cable C by the cable extending through the sampler post and a centrally-located aperture 54, 56 through each disc and spacer, and by the weight being tied or otherwise attached to the cable.

FIG. 5C is an exploded view of the three sensor discs 50 and two spacers 52 of FIG. 5B, wherein the spacers are for cushioning and protection from friction and wear and/or for electronic/electric insulation and/or static prevention.

Figure 6A:
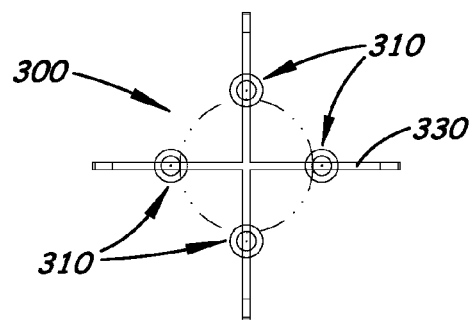
FIGS. 6A, 6B, and 6C are top, side perspective, and side views, respectively, of a sampler system according to another embodiment of the invention, wherein four strings of samplers plus sensor discs hang between X-shaped brackets at or near a top support/anchor-point and a weight. One string of samplers hangs from each of the four arms of the X-shaped bracket, with one of the strings of samplers being hidden in back of the front string of samplers in FIG. 6B. The multiple strings of samplers may be used for testing of the same area of the environment at various times and at various depths. For example, one string may be pulled at each of four times, for example, a first string 8 hours after a treatment with herbicides), a second string at 24 hours after treatment, a third string at 48 hours after treatment, and the fourth string at 72 hours after treatment.
Figure 6B:
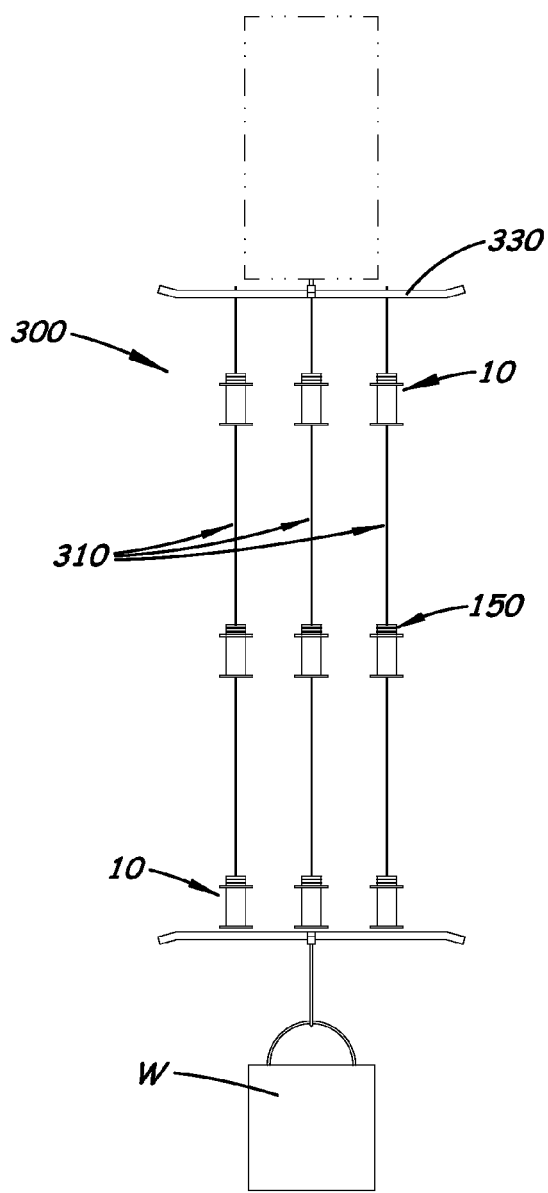
Figure 6C:
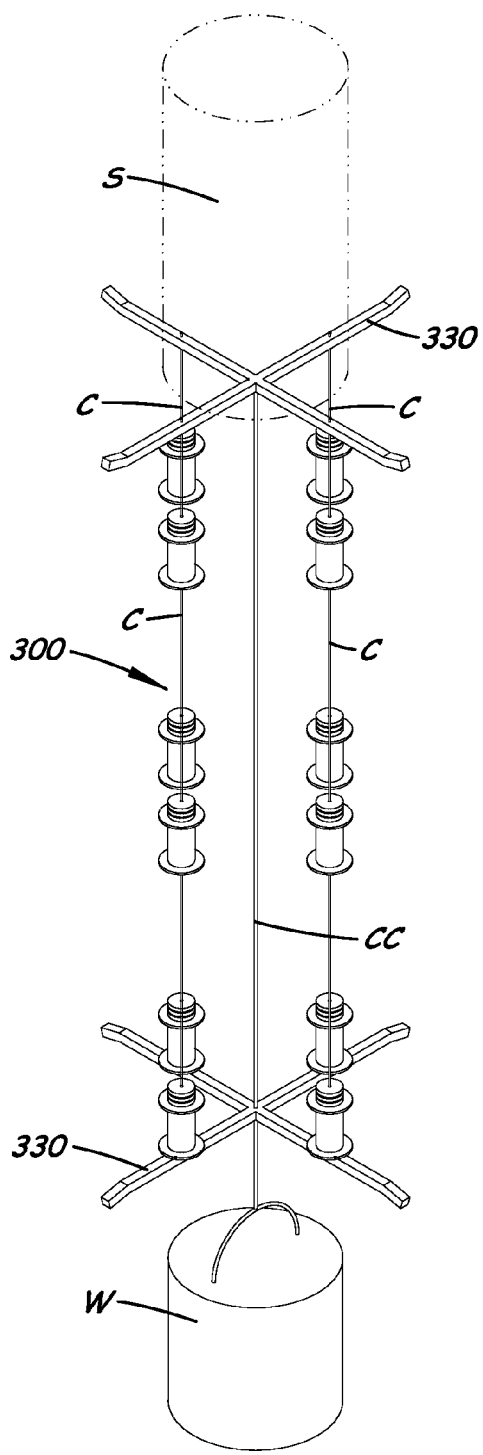

FIGS. 6A-C show a sampler system 300 wherein four sampler strings 310 of samplers 10 plus sensor disc assemblies 150 hang between X-shaped brackets 330 at or near a top support or top anchor-point S and a weight or bottom anchor-point W. The X-shaped brackets 330 are connected to the top and bottom of each cable C to keep the strings of samplers separated from each other in a predetermined arrangement and spacing. A central cable CC may extend between the X-brackets and/or between the top and bottom anchor-points S and W, to strengthen the system 300. One string of samplers hangs from each of the four arms of the X-shaped bracket, with one of the strings of samplers being hidden in back of the front string of samplers in FIG. 6B.

FIG. 7 portrays a sampler system 400 that includes a solar-powered and telemetry-and-GPS-enabled buoy B, a cable extending downward from the buoy, and two transverse tethers T and samplers 10 extending out from cable C. The two tethers T extend from points part-way along the length of the cable C to tether two samplers 10 with sensor disc assemblies to the main cable, in a configuration that allows the samplers and discs to float generally horizontally out from the main cable. This way, the current in a waterway will send each sampler and its discs downstream, at different depths, a distance generally equal to the length of its tether. FIG. 7 shows the two tethers to be about equal, but tethers of different lengths may be beneficial to test/monitor water at different distances from the single buoy and weight assembly.

FIGS. 4-7 portray sampler systems/assemblies wherein the samplers are suspended in water and anchored by a weight or other anchor-point. In other embodiments of the invention, however, the sampler system/assembly may be suspended from a buoy but allowed to float free with currents, or with the tide and waves in salt-water/ocean environs. Such free-floating embodiments may be unweighted, or may have some weight that keeps the string/assembly of sampler(s) generally vertical, but not so much weight that the sampler system/assembly is anchored only in one place in the water.

FIGS. 10A and B portray one, but not the only, embodiment of a stake or spike-type sampler system. The screw-in stake sampler system 500 of FIGS. 10A and B. These sampler systems may be installed in the ground, for example, in soil, sediment, gardens, or agricultural regions. These samplers rely on liquid in the soil/sediment, including liquid seeping down into the soil-sediment, to flow into the sampler and/to contact the sensor discs to contact the resin/adsorbent and the sensor materials/membranes.

The stake sampler system 500 includes a stake 505 that holds one or more samplers 10 and preferably one or more discs for insertion into soil or sediment to place sampler(s) below ground. The top end and handle 515 of the stake may be detached from the lower, cork-screw-style end 525 of the stake by a quick-connect or other connection 530. This detachable connection allows the sampler 10 to be removed and/or emptied for analysis of the resin/adsorbent. The connection 530 or other provisions on the stake should be designed so that the sampler and discs are held in place near the lower end 525 of the stake, so that screwing the stake into the ground (soil/sediment) will not allow the ground to push the sampler and discs up toward the handle end 515 to be out of, or higher than desired in, the ground.

The sampler system in FIGS. 10A and B are an example of a sampler system/assembly that may be deployed below ground surface to collect and measure the downward migration of pollutants or environmental contaminants for sediment measurements. A stake or spike-style sampler may contain specifically-formulated ion-exchange resins tailored appropriately to collect and measure herbicides, pesticide, heavy metals, organic compounds, radionuclide's, or other unique pollutants or environmental contaminants of concern contained in run-off water. An adaptation of this embodiment may include an optional base B" holding GPS transmitter and telemetry above the handle end to provide real-time data and positioning, as described elsewhere in this document.

FIGS. 11A-C portray two, but not the only, embodiments of a "run-off box" embodiments, which may be placed on a hill-side or shore to capture water run-off from the surrounding up-hill area. A fixed collection box system such as sampler system 600 can be located in the environment to sample runoff and subsequent leaching from waste sites and suspect contaminant areas. In this example, the samplers are placed within the collection box and runoff is allowed to flow into and through the container. The container can be made into any size and shape. The container holds the sampler(s) in a fixed position which is normally at the low point of any expected flow and allows the runoff to run into and then exit the container. Contaminants are adsorbed onto the resin and the sensors can be used to track key environmental indicators. This device is ideal for areas where runoff from waste sites or areas is suspected to contribute to damage to the surrounding area and environment (runoff into ponds, lakes, streams, sewer systems or to unsuspecting landowners). The user can place this container in an area of suspected flow/runoff and simply check the samplers on a monthly basis. One such example would be in the Canyons around and adjacent to the Los Alamos site in New Mexico. Flooding from summer storms hit the plateau where the waste sites are located and runoff then flows through the canyons into streams and eventually the Rio Grande River.

The run-off sampler system 600 comprises one or more box-like containers 605 that may be set on a hill-side or shore, to receive water running-off land to a lower region and/or a water body, for example, from a waste-contaminated area WA. The run-off will enter the container to contact one or more samplers 10 and preferably discs inside the container(s). The container may be set on or shallowly in the ground, in which case, the openings 615 in the container will tend to be low on the container. Alternatively, the container may be deeper, in which case lower openings 615 will tend to capture water deeper in the hill-side/shore, or openings may be provided elsewhere in the container. The samplers and discs may be provided in a stand or other holders inside the container, and the container may have a lid, for removal of the samplers.

COMMENTS AND EXAMPLES

The above-described sampler systems and certain other sampler systems of the invention allow retrieval of the samplers and/or the resin/adsorbent for laboratory analysis of the elements, compounds, or other contaminants or molecules adsorbed or otherwise captured by the resin/adsorbent to provide data from various locations in the environment. Said various locations include various depths in water or heights in the air, and over various amounts of time based on the placement and retrieval schedule for the samplers. Decision-makers responsible for natural resource damage assessments may benefit from the combination of extended-time adsorbent(s) in the samplers, plus the preferred telemetry/GPS-linked remote sensor discs, because the combination provides an assessment team with real-time response data (such as dissolved oxygen, pH, temperature, soil moisture, and/or other remote sensing) plus "accumulated data" (contaminant identities and concentrations achieved by extended-time contact of the adsorbent(s) with the environment) from the ion-exchange/adsorbent samplers.

Embodiments of the sampler system may be used for water, soil, sediment, air, and gaseous emissions studies, in any medium that allows contaminants to pass into the sampler to contact the resin/adsorbent. The sampler system may be used, for example, for water quality determination and remediation in watersheds, water bodies such as lakes, reservoirs, streams, bays, marshes, saltwater, fresh water, surface-water run-off, and sewers or storm drain systems. The sampler systems may be used, for example, for air quality determination and remediation in neighborhoods and industrial sites. The sampler system may be used, for example, for soil or sediment monitoring, for example, in river-beds, along shore-lines, and near waste disposal and industrial sites. The sampler system may be used, for example, in agricultural regions, for monitoring of pesticides and herbicides and fertilizer run-off, and other chemical issues. The sampler system may be used, for example, for Publically Owned Treatment Works (POTW) and National Pollutant Discharge Elimination Systems (NPDES) discharge. The sampler system may be used, for example, to monitor dangerous or illegal effluents, either liquid or gaseous, from homes or other buildings, for example, by positioning samplers in a sewer system, in trees or other locations.

In the case of water monitoring, use of certain embodiments of the invented system may be used as a supplement to, or instead of, the conventional method of taking grab-samples of water in the case of water monitoring, and thus may improve monitoring of water quality, contaminants, and other environmental issues. These improvements may result from the sampler being in contact with the water or watershed over an extended period of time, instead of only taking a small "spot sample" associated with an instant in time. The sampler system may be left in contact with the water/watershed for hours, days, or weeks, during which time the preferred real-time sensors may stream data on pH, oxygen, temperature, and in some embodiments chemical detection data, for example, to the monitoring research station, and, after which time, the ion-exchange resin sampler may be retrieved and studied. This combination of data, that is, streamed data over time, plus analysis of the ion-exchange resin sample that has contacted said water/watershed over generally the same amount of total time, provides an improved "view" and understanding of the environment being testing. The sampler system allows these dual modes of testing, and this resulting improved view/understanding, with surprisingly simple sampling and sensing equipment that is adaptable to many different environments and to a large area and volume of said water/watershed. The ability to test a large area and volume, with multiple samplers over an extended time, and the ability to compare the sampler system data to grab sample data, further enhances water quality testing and monitoring.

Users of the invented system may have the benefit of time-measured mass-balance data sets, using the time-accumulated values of contaminants/chemical determined by laboratory analysis of the ion-exchange resin that has been left in place for hours, days or weeks/months to accumulate contaminants. Also, the users may have data from the real-time sensor discs that report environmental conditions or other physical or chemical conditions for recording over said hours, days, or weeks/months, preferably via a real-time telemetry and GPS system communicating with the laboratory or monitoring headquarters. Said telemetry preferably comprises one or more wireless data transfer mechanisms (for example, using radio, hypersonic or infrared systems), but may also or instead include data transferred over other media, such as a telephone or computer network, optical link or other wired communications.

The preferred cylindrical design allows the sampler to be inserted on a cable, rod, frame member, or other support member, for placement in water or another area to be studied. Cables, with an optional weight near the end of the cable, may be optimal for testing/monitoring a body of water, as gravity will maintain the desired orientation of the cable, samplers, and sensing discs. Rods or rigid members may be optimal for testing/monitoring a sewer, marsh, or other area that require, or are tested better with, more control of placement initially and throughout the extended testing period.

For most of the uses listed herein, the sampler will be made out of a chemical-resistant plastic that is compatible with the necessary leaching chemicals to extract the contaminants from the ion-exchange resin in the lab. Optionally, the sampler may be made to be disassembled, either in the laboratory or at the environmental site, so that the packets/sleeves or granules may be removed and replaced with fresh resin/adsorbent.

The sampler ion-exchange resin or other adsorbent, and the optional but preferred sensor discs, will be selected and tested for adsorption and detection, respectively, of various contaminants/chemicals, to match the needs of the client and project. Examples of possible contaminants and environmental applications for the invented environmental sampler include the following: petroleum and petroleum by-products; heavy metals; organics; items of interest for national security; other organics (volatiles and semi-volatiles); radionuclide analysis; nutrient run-off (hypoxia studies); bacteria indications; herbicide and pesticide applications; trace contaminants such as fisheries and water quality analysis; tracking by products of illegal drug manufacturing (e.g. "meth" by-products being illegally discharged into a cities waste water treatment facility); and/o trace chemical elements associated with climate change efforts within environmental media.

A single resin/adsorbent may be provided in a single sampler or in multiple samplers, wherein the resin/adsorbent is provided as loose granules/particles or in one or more packets. If multiple resins/adsorbents are used in a given sampler, the resins/adsorbents may be mixed together or layered in multiple beds, or housed in separate packets/sleeves, or connected packets/sleeves, according to a customized testing composition and plan. All the samplers for a given environmental media may contain the same resin/adsorbent or some or all of the multiple samplers in that environmental media may contain different resins/adsorbents. Packets/sleeves may be made of permeable fabric/material that is packed with the resin/adsorbent and slid inside the sampler, with the packets/sleeves optionally containing multiple compartments, for example, by compartments being sewn or otherwise connected.

One or more samplers may then be placed in the environmental media (the water, liquid, air, gasses) at pre-selected depths and locations, by means of a retrievable support system. Typically, multiple samplers containing the same composition(s) and arrangement of resin(s) will be installed in the environmental media at said pre-selected depths and locations, in order to "view" the various locations in the environmental media over the extended time period with the same resin(s)/adsorbent(s). "Retrievable" means that the user may retrieve each and/or all samplers at the desired time from the environmental media, by lifting, reeling, or otherwise extracting the support structure, to which the samplers are attached, preferably by pulling the support system. The support systems typically will be categorized as tethered systems or fixed systems. In tethered systems, the samplers are connected to a cable or flexible support, using a weight or other attachment to a peripheral structure so that the cable/flexible support does not float significantly out of the desired depth/location. In most tethered systems, the samplers are held generally in place, but some movement may be experienced due to currents and or waves. In a fixed system, the samplers are fixed to a rod, frame, or other rigid structure and will tend to move very little or not at all relative to the environmental media.

Tethered or fixed support systems may be pulled or otherwise extracted by means of manual or mechanized pulling (or less commonly pushing) of said support structure. Both tethered or fixed systems allow the system to be placed in fixed or substantially fixed locations from which the sampler(s) can be easily retrieved following the sampling campaign.

Examples are shown below of how embodiments of the invented system may help in current challenges presented to the communities world-wide.

Example I

River and Tributary Management

In FIG. 8 there are schematically depicted locations of samplers 10 according to one, but not the only, embodiment of the invention that may be placed in rivers R and tributaries T for watershed management. Samplers containing ion exchange resin(s), remote sensing discs, and telemetry apparatus are suspended along a cable from a buoy and anchored in the bottom sediment of the river and tributaries. Samplers suspended within the water are arranged at various locations within the watershed area, for example, on one or more cable systems such as those discussed earlier in this document. Sampler systems such as those drawn in FIGS. 4-6, and 7 are candidates for this river and tributary environment. The transversely-orientated samplers in FIG. 7 may work well in such an application, due to the currents of the rivers/tributaries.

Sampler positions are used to establish baseline ecological conditions and to identify sources of environmental contaminants or pollutants. In this embodiment of the invention, multiple samplers may be suspended from the cable with each sampler containing specifically formulated ion-exchange resins tailored appropriately to measure nutrient loading, herbicide, or pesticide concentrations, heavy metals, organic compounds, radionuclides, or other unique pollutants or environmental contaminants of concern.

Example II 2-4-D Application for Treating Noxious Milfoil within Lakes and Watersheds In a lake or other water body WB, schematically portrayed in FIG. 9, samplers 10, including single samplers but more preferably assemblies of samplers, may be placed at multiple depths along one or more cables, for example, as in the configurations shown in FIGS. 4 and 6A-C. Multiple cables and/or assemblies of cables allow redundant data, data in various locations in the lake/watershed, and/or time-phased data collection. Samplers can be suspended in a lake or other aquatic environment to manage application and treatment of noxious aquatic vegetation (e.g., Milfoil). Samplers are used to determine concentration and dispersion (both surface and depth) of 2-4-D or other herbicides used to treat Milfoil, specifically the amount of herbicide available for uptake by the Milfoil. Samplers may be placed outside a Milfoil-treatment zone Z of the water body WB, as well as inside the zone Z, to monitor movement of herbicides from the zone. Over time a (e.g., 8 hrs, 24 hrs, 48 hrs following treatment application), samplers may be removed and analyzed to evaluate time-phased dispersion and concentration.

For redundant data, the user would lower/install cables in close proximity to each other, wherein each cable would have samplers and discs at generally the same level (for example, 5 feet, 10 feet, 15 feet, and 20 feet, for example). For time-phased date collection, cables could be lowered at different times, and/or far apart in different locations that are expected to be in the flow path of a chemical or contaminant, for example. Or, different resins/adsorbents may be put in the samplers of different cables, but preferably with the cables close together, for adsorbing different chemical/contaminants at generally the same place at the same time. Depicted in this embodiment are samplers suspended in a lake or other aquatic environment to manage application and treatment of noxious aquatic vegetation (e.g., Milfoil). Samplers are used to determine concentration and dispersion (both surface and depth) of 2-4-D or other herbicides used to treat Milfoil. Over time (e.g., 8 hrs, 24 hrs, 48 hrs following treatment application), samplers are removed and analyzed to evaluate dispersion and concentration, that is, the location and amounts of chemical(s)/contaminant(s). Remote sensing discs (to measure physical parameters such as, but not limited to, dissolved oxygen, pH, and temperature) may be added to the cables, with one of each type of desired sensor preferably located at or very near a sampler, so that the data from the sensor discs sent by telemetry may be associated and correlated with the laboratory analysis of the resin/adsorbent from the respective sampler.

Example III

Figure 12A:
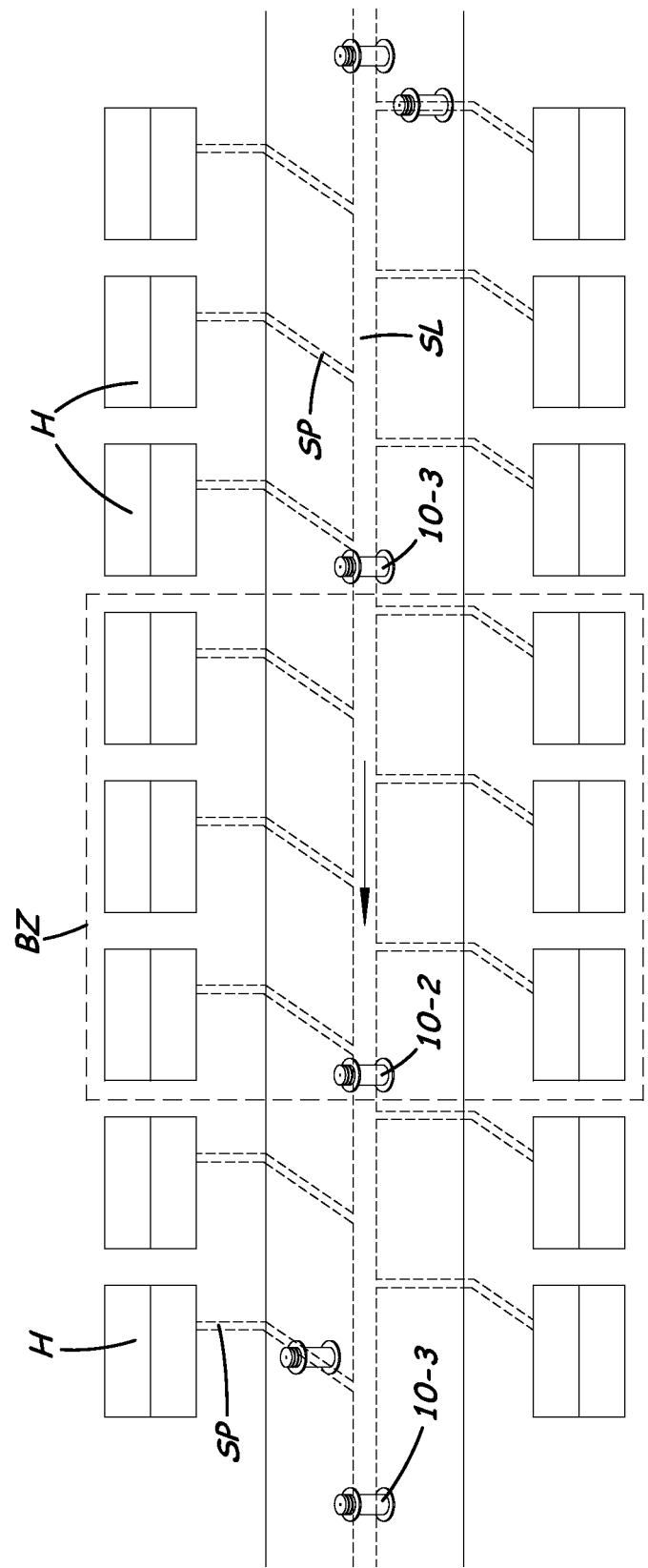
FIG. 12A is a schematic that depicts multiple samplers deployed in a residential sewer system to monitor for chemical and chemical by-products from multiple building (square blocks) potentially associated with the production of illegal drugs, or other dangerous or illegal discharge.

Detection of Methamphetamine Production or Other Chemicals of Concern in Sanitary Sewer Systems As shown schematically in FIG. 12A, samplers, including sampler assemblies of samplers, may be placed in commercial and residential sewer pipe to monitor discharge or contaminants of concern, including environmental pollutants associated with NPDES and POTW monitoring. The samplers may be placed in the sewer pipes HS from individual buildings or homes H, and/or in the main sewer line SL. One example is the identification of methamphetamine and by-products associated with its manufacturing. Waste water treatment plants across the U.S. cannot treat for every illicit drug and/or residual pharmaceutical compounds. Municipalities have to dilute and blend water from the treatment facility rather than incur costly treatment systems. The accumulation of compounds is causing grave concerns within municipal watersheds, and traditional sampling methods are primarily grab samples that only capture the compounds in the flow at the brief time of sampling. Samplers according to embodiments of the invention, containing specifically-formulated ion-exchange resins may be used as a positive indicator for items of concern.

As shown in FIG. 12A, sampler(s) may be provided in individual sewer pipes SP from suspect or previously-problematic buildings, to test the effluent from the building. Or, sampler(s) may be placed in the main sewer line SL, at predetermined intervals, so that detection of chemicals by a particular sampler (for example 10-2 in FIG. 12A) but not by sampler 10-1 and to a lesser extent sampler 10-3, will indicate that the source of the chemicals is likely to be building zone BZ. This way, sampler placement may help narrow the many possible problematic discharge points, to a determination of one or a few suspected or determined point(s) where problematic chemicals and/or chemical by-products are being discharged to the sewer.

Figure 12B:
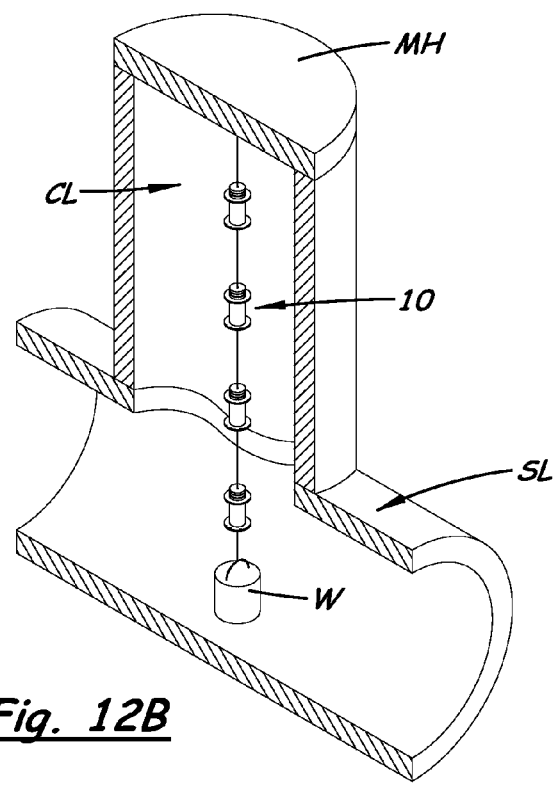
FIG. 12B is a side perspective view showing a sampler with discs embodiment that may be placed in a sewer cleanout or other access to a sewer/storm-water system, wherein samplers may be positioned both in a horizontal portion and a vertical portion of the sewer/storm-water system.

As shown in FIG. 12B, samplers may be lowered through a man-hole or cleanout structure CL that may comprise a vertical pipe tied to a manhole on a street, alley or parking lot. The sampler(s) may be affixed to a cable or threaded rod and lowered into the effluent stream within a horizontal pipe/sewer-line. A single sampler may be provided in the horizontal pipe/line, or multiple samplers may be provided at various levels relative to ground level to measure/monitor sewer liquid composition/contaminants during normal low-flow conditions and/or high-flow conditions. This way, one or more samplers may contact the effluent that flows through the pipe and into a waste water treatment plant or discharged to an approved source (as listed within an approved permit). The sampler(s) may be fixed to, or weighted to rest in, a position such as the low flow point within the pipe to capture contaminants of interest such as heavy metals. Or, the sampler(s) can be allowed to float within a range of flow. In the case of a floating sampler(s), the sampler(s) will float on the surface and can then be used to detect organics and materials that have a specific gravity less than water and, therefore, would be expected to be floating on the surface of the effluent stream of the waste water. The sampler(s) is/are retracted from the pipe/line, so that the used resin can be removed for analysis, and the resin can be replaced with fresh resin; this way, the sampling campaign can continue uninterrupted allowing for 24/7 detection of contaminants.

Figure 13:
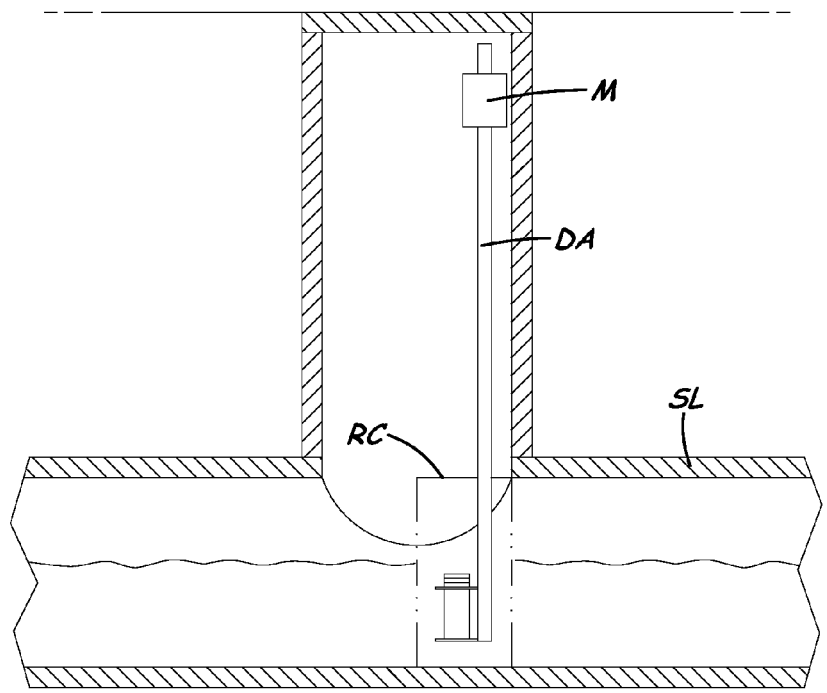
FIG. 13 is a side, partially-cross-section view of the sewer/storm-water system of FIG. 12B, wherein a sampler with discs is lowered and retrieved by a motorized arm, and wherein the sampler and discs are provided in a retention cage in the horizontal portion of the sewer/storm-water system whereby the sampler with discs may float with the liquid level.

A specialized mechanism may be used to deploy certain embodiments of samplers in a pipe or underground vessel. For example, as shown in FIG. 13, a specialized deployment arm DA driven by a motor M may move one or more samplers to the bottom of the sewage line, thus, placing the sampler into the discharge flow. The sampler may be left in the low flow section of a sewer system and can detect the discharge of contaminants 24/7 to allow agencies to pinpoint areas of concern for compliance. To create a floating embodiment, the sampler may be contained in a retention cage RC that retains the sampler in the cage but lets it float up and down to some extent with the liquid level in the sewer line, as discussed above.

Samplers may be used for, but not limited to, measuring for illegal drug related by-products nutrient loading (such as Hypoxia concerns in watersheds), herbicide/pesticides, heavy metals, organic compounds, radionuclide's, and chemicals and chemical by-products important that are a concern to national security, drinking water safety, and/or other concerns. An adaptation that includes remote sensing discs may include the measurement of pH, conductivity, organics and chemical indicators such as nitrogen and phosphorus.

An adaptation could include remote sensing discs, similar to those discussed above, to measure pH, conductivity, organics and heavy metals and to send measurements/data by telemetry to a lab, headquarters, or other distant facility.

Example IV

Ion Exchange Resins for Organic Elements

Applications may include the selection of ion-exchange resins for organic elements, for example, a resin such as "Ambersorb 575" which is a synthetic adsorbent that works well for organic materials and solvents, "Amberlite XAD7HP" resin is used for a wider range of organic materials, and a compound such as "Ambersorb 563" works equally well for organics although it is harder to recover. Typically hot water or alcohol is used to extract the compounds from the resin. In this example, the ion exchange cylinder (sampler cylinder) would be placed in the top layer of the watershed allowing the resin to come into contact with the compounds of interest. Without a specific compound of interest, Ambersorb 575 could be combined with Ambersorb 563 to create a blend for a wide range of compounds. The resin sampler would be replaced every 7 days allowing for an evaluation of damage and/or impact to the environment. Continual baseline assessments would be the goal to evaluate natural attenuation and/or remediation and treatment efficiencies for the area being evaluated.

Remote sensing systems for dissolved oxygen, temperature, conductivity and oxidation and reduction potential sensors can be used to present a subset of environmental conditions that will provide useful data associated with water quality and the general health of the environment.

Example V

Heavy Metals

In this example, a resin would be selected for a watershed next to an environmental cleanup site such as mine tailings adjacent to a stream. In this instance, a resin may be selected that is titled "Amberlite IRN-150" and is used for inorganic and specifically for heavy metals. The samplers would be attached to the buoy system, however, depths of resin samplers would be varied to ensure that one sampler is placed at the stream bottom due to the density of the heavy metal particulates. Once again a baseline sampling campaign would be conducted allowing for the removal and replacement of the resin sampler every seven days. In this case, it may be elected to place additional samplers within a near surface collection container within a valley or canyon at a higher elevation than the streambed. Additionally, it is likely that multiple samplers could be placed within the soil and near surface vadose zone to track the presence of existing contaminant migration efforts from the site in question.

Remote sensing systems that could compliment the evaluation may include sensor discs for pH, temperature, dissolved oxygen, turbidity, total suspended solids (TSS), ammonium, and oxidation and reduction potential, to assist in tracking the metallic pollution of surface and groundwater sources.

Example VI

Air and Gaseous Emissions Monitoring

Figure 14:
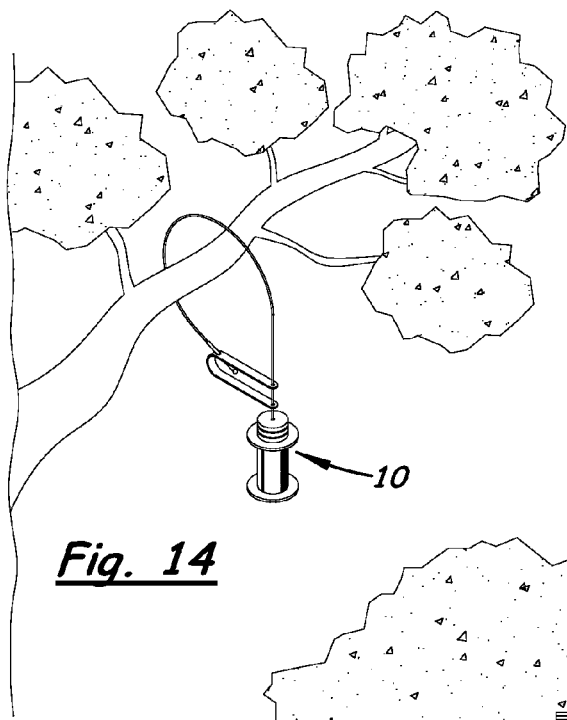
FIG. 14 shows an alternative embodiment wherein a sampler is hung in a tree to monitor air quality, for example, general air quality or pesticide content.
Figure 15:
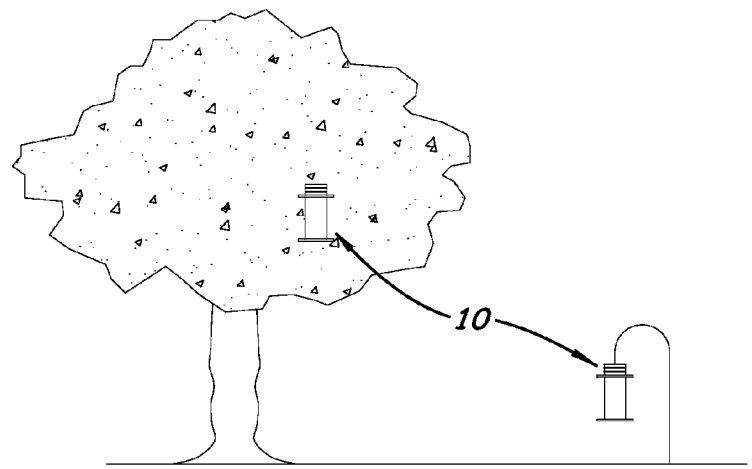
FIG. 15 portrays an embodiment of an air sampler provided in a tree and an air sampler on a hanger installed in the ground.
Figure 16:
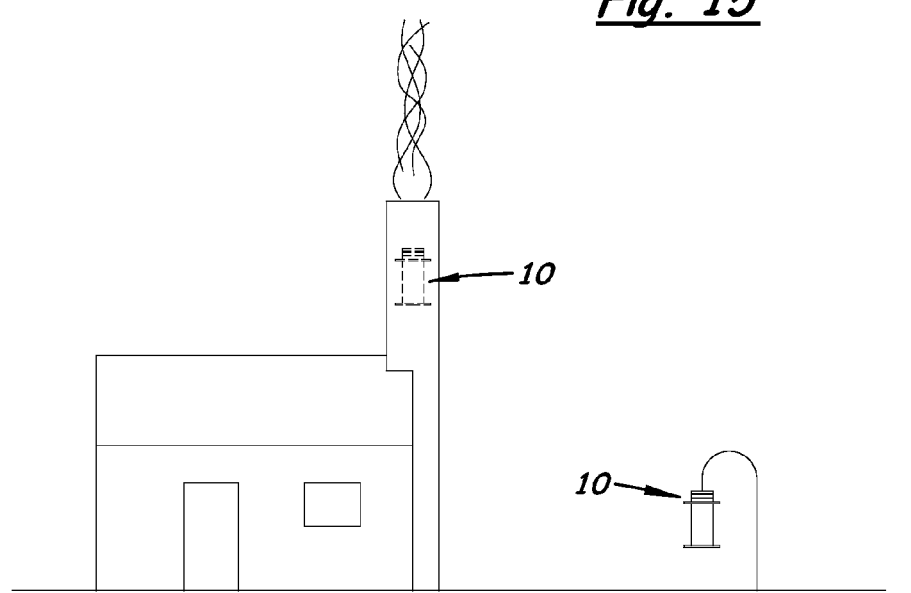
FIG. 16 portrays an embodiment of an air/gasses sampler in a smoke-stack/chimney, and an air sampler on a hanger nearly.

FIGS. 14-16 depict samplers provided in air and/or in places wherein contaminants enter the air. FIG. 14 shows a sampler with sensor discs hung in a tree, for monitoring air quality. FIG. 15 shows sampler with sensor discs both in a tree and hung nearby by a hook or other hanger provided in the ground. FIG. 16 shows a sampler provided in a smokestack of a factory/utility to measure a continuous as well as an intermittent discharge event(s). Also in FIG. 16 is shown a sampler hanging from a hook provided in the ground to monitor air quality down-wind of the factory/utility. In these and other ways, samplers preferably with discs, may be suspended in residential areas, agricultural areas, forest or primitive areas, and/or in industrial areas, to monitor air general quality and specific emission sources. In industrial areas, samplers may monitor stack/chimney, vents, and/or flares that emit discharges associated with applicable air monitoring permits, and other discharges associated with unwanted discharge to the environment (e.g. global warming).

Samplers may be configured to measure environmental parameters such as gas-phase release measures associated with manufacturing industries, herbicide/pesticide application including drift studies, organic compound releases, and radionuclides. As discussed above in this document, remote sensing discs may allow for the monitoring of physical parameters such as oxygen, CO2, pH, and temperature, and GPS apparatus and telemetry can provide real-time data and positioning. Telemetry may be used to integrate a system of samplers and remote sensor discs to provide real-time composite data over large geographical areas.

Example VII

Time Release and Phase Detection Studies

Embodiments of the invention may provide capabilities for time release and phase detection studies, by using the embodiments to include comparing standard grab sample data to the extended-time data obtained with the embodiments of the invented system. Said extended-time data available from embodiments of the invention may include adsorption of particular chemicals/compounds by the resin/adsorbent in the sampler (tested later or intermittently at the lab) and may also include real-time sensing of the same or related chemical/compounds by the sensing disc (data received by telemetry over the extended period). This is made possible by obtaining real-time sensors that are designed to sense the specific chemical/compounds of interest, or to sense groups or general types of compounds in which the chemicals/compounds fall.

Examples of specially-adapted real-time sensors would include sensors for chlorine, chloride and chlorophyll compounds, used as an indicator of algal biomass and indicative of wastewater from industrial and NPDES/POTW facilities. Nitrate and nitrogen sensors may be used to evaluate nutrient loading associated with excess fertilizer applications and bacterial investigations, while suspended particulates, turbidity, total suspended solids (TSS) are also used as general sensors as an indicator of health and changing conditions. Phosphorous and nitrate sensors may indicate the presence of organic wastes and stimulate overproduction of aquatic plant growth when present in elevated levels. Ammonium sensors can be used for the evaluation of water quality for fisheries since small amounts are very lethal for species such as trout. Additionally, ammonium may indicate a discharge of waste water from septic systems, fertilizer runoff or sewage treatment facilities. Sensors of pH may measure the amount of hydrogen ions present and present an indication of the acidity of a substance. Conductivity sensors can be used to indicate environmental events such as underground fresh water aquifer near the ocean that could be an indication of salt water intrusion. Oxidation and reduction potential can be measured and can be used to correlate the life expectancy of bacteria in water supplies and are useful to track the metallic pollution of surface and groundwater sources.

Concentration-based data collected by remote sensing discs and parts per million concentrations within the ion-exchange resin is normalized against contaminate concentration per volume obtained through standard grab samples. The ability to compare concentration per volume within a grab sample to the remote sensing disc data and ion-exchange resin data allows the end users to compare and contrast the data in respect to time release, contaminate buildup, and phased detection of chemicals and contaminants of concern. Phase detection is the normalization of data sets by comparing the affinity of a chemical to a given resin type within the invented sampler. The phase detection study is relevant since each chemical (contaminate) is attracted to a given family of resins and resin types. Typically one resin is selected that allows for the detection of specific contaminants of concern that are similar in their nature (e.g. inorganic heavy metals). By understanding the affinity of a resin with the targeted chemical one can extrapolate contaminate concentrations measured in the invented sampler to real-world environmental concentrations.

Other time release/phase detection studies will be designed to understand how specific ion-exchange resin in the invented sampler reacts with a surface floating organic substance as compared to the same substance in a different phase within the same environmental media. For example, crude oil on the surface of water will be detected by the invented sampler at a different concentration than the conglomerate of crude oil, dispersion chemicals, and water at depth (e.g., surface oil and a mixed compound of oil and dispersion chemicals currently being seen in the recent Gulf Oil Spill).

Example VIII

Time Release Buildup

Time release build-up refers to the ability of embodiments of the sampler resins to capture contaminate ions and cations over a pre-defined time period. The use of the preferred ion exchange sampler provides a data gathering platform not otherwise available. The preferred cylinder design, and preferred cylindrical or bendable/foldable bag, sleeve, or other packet(s) containing the resin, maximize contact of the resin with the environment and maximize contaminant uptake by the resin. Resins are selected to target specific chemicals based upon their charge and affinity to a resin or a blend of resins. Proper environmental management requires decision-makers to have an understanding of how environmental contaminates change over time. The invented system is capable of discriminating contaminate uptake over time. Current EPA sampling methods are highly focused on grab sampling techniques that do not consider the effect on natural resources by very small incremental buildups of contaminants and trace chemical elements.

The preferred cylinder sampler design also provides an improved engineered contaminate collection platform that allows precise placement of the samplers into environmental media not otherwise readily achieved. One such condition is Hypoxia studies that take a look at micro nutrient transfer and buildup in aquifers or watersheds that result in harm to natural resources. Measuring the slow, time dependent buildup of chemicals on a continuing basis can all be readily addressed with this system, for example, including consideration of various release mechanisms such as a) illegal discharges, b) high flow and flood release events such as runoff from surface agricultural areas and c) very small concentrations that accumulate over long periods of time. This may also include the ability to use the invented sampler as a detection tool that can obtain contaminant measurements from a "non-detect" condition as measured by traditional sampling methods.

Example IX

Time Measured Mass Balance Data Sets

One of the simplest ways to describe the usefulness of the data is to consider the use of time-dependent data sets. Within the field, users can build mass balance buildup of contaminants and understand chemical release/buildup curves by understanding 2-day, 5-day, and 10-day data sets. This would involve installing multiple samplers in the environmental media and retrieving sampler(s) at each of the 2-day, 5-day, and 10-day marks, and comparing the resulting data to the real-time data achieved from the sensor discs, and preferably also comparing to the data achieved from grab samples spaced throughout those time periods. When end-users understand the buildup or release mechanisms as a function of time, flow and other environmental variables (temperature, pH . . . ) they can correlate the data into improved data sets.

Standard methods for accumulation and consideration of data sets are based on methods that cannot provide an easy and cost-efficient manner for comparison. For example, recent concerns with unwanted algae growth within watersheds result in decision-makers trying to correlate how miniscule amounts of contaminants interact within the environment and contribute to unsafe water supplies and the loss of recreational opportunities. If regulatory agencies implement tools such as embodiments of the invented sampler system, they may obtain real-time data with the sensor discs and can readily complement and compare/contrast standard sampling techniques (e.g. an EPA test method), and preferably also compare/contract said real-time data and said standard sampling techniques (such as the EPA test) to the ion-exchange resin sampler data.

Users of the sampler can use the knowledge gained by time-measured (for example, 2, 5, 10-day data sets) and mass-buildup (e.g. the slow accumulation of chemicals and contaminants within the resin) to grasp and understand the problem statement/area. Once an agency or concerned party understands that 90% of the problem is coming from a problem such as leachate of contaminants from near surface septic systems on the waterfront or from unwanted discharge to a watershed from a dairy five miles away, for examples, they can focus their attention on the solution. The advantage with certain embodiments of the sampler is the detection is continuous and not intermittent as with other systems. In addition, resin blends can be developed by the laboratory and independently tested to confirm the use of modeling means and methods.

Another example is the release of bacteria and micro nutrients from agricultural areas that feed into a watershed that may be "non-detect" using conventional systems, but can be measured and quantified by a remote system that includes embodiments of the invented system to measure small increases of contaminates over time. If a state agency or environmental manager knows that an algae bloom is due to five times the concentration of nitrogen, phosphorus and other compounds of interest from a specific streambed, they can concentrate corrective measures in that part of the system. The same is true in the areas where waterfront septic systems are failing, leaching into aquatic environments, and contributing a significant contribution of problem contaminants. By placing embodiments of the sampler systems in core locations on the waterfront, they can compare 7-10 day data to monitor and document the relative harm to the natural environment.

Example X

Ion Exchange Resin Manufacturers and Resins Selection

Currently over 900+ types of resins manufactured worldwide. Strong or weak resins are specifically selected for their affinity to attract cations and anions of concern. There is a unique science associated with the selection and blends of resins that can be created (see below) to target groups of contaminants, and more preferably subsets of or individual contaminants, of concern.

Resins and resin blends may be selected and tested based upon the affinity to attract certain compound(s), or compounds groups, of interest. Many resin and resin blends will work and selection of many resin and resin blends will be within the average skill in the art without undue experimentation.

Example XI

Sensors and Sensor Signal Transmission

The preferred real-time sensors may be similar in design to conventional sensor probes. Some real-time sensors are set for wireless operation, while others have hard wires to the telemetry system (wireless vs. wired is primarily a cost issue). Many real-time sensors that will be effective in embodiments of the invention are commercially available and obtainable by those of average skill in the art.

Wireless and wired systems can be manufactured and used that rely on remote telemetry or wireless internet access. Standard, known techniques for remote transmission of data may be used.

Example XII

Advantages to Cylindrical Container

The preferred cylindrical system is not affected by orientation and provides 360 degrees of coverage within an effluent stream or other environmental media. The hollow stem allows the cylinder to be used with different support systems depending on the environment and deployment/access options. The hollow passageway of the sampler stem/post may be sized relative to the support system so that there is a tight fit between stem/post and support system, but many embodiments will also or instead have a fastener to fixedly connect the sampler to the support system so that it doesn't slide or fall relative to the support system. Some fasteners will allow rotation of the sampler around the support system (cable, rod, arm) but not axial sliding or falling. The preferred cylindrical design for the resin sampler and the sensors dics allows for precise placement in wastersheds and effluent streams, wherein orientation (rotation) of the cylindrical shapes around their axis is not a problem or an issue.

Another major advantage of the cylindrical sampler shape is that packets of ion exchange resin can be readily changed out by disassembly of the cylinder housing and pulling the packets axially out of the housing screen. These removable packets are design to allow for rapid and complete extraction of the chemical from the resin in that acids, solvents, and other materials can be safely used and the packets of resin placed underneath a drip system or inserted into a bath for extraction and removal of the target elements from the resin. The sampler housing design allows for fast insertion and removal of multiple, different, interchangeable resins into the same ("universal") cylindrical housing.

Shapes other than cylindrical will work for alternative embodiments of the ion-exchange container and the sensors. For example, spherical, oblong, or rectangular sampler housings may be used. However, the cylindrical design is preferred to 1) allow maximum contact with the environmental medium being sampled and 2) to accommodate a variety of engineered support and retrieval platforms to address multiple environmental media and deployment options. The cylindrical design allows contact over 360 degrees while allowing the resin sampler to be mated with the sensing discs in coaxial relationship and closely-axially-adjacent. The hollow cylindrical sampler housing allows for insertion upon a cable or other axially-extending device. In addition, the hollow axial passage through the housing allows other types of fixing/attachment to a support/retrieval platform, for example, providing a cable, wire, or bracket through the passage that is then tied or otherwise fastened to the platform. A major shape advantage to the cylindrical sampler and circular-disc shapes is that these shapes provide very long-term use in the environment though the resin-containing spaces, and membrane or sensor probe-containing shapes are compact; this reduces the size and diameter of the sampler and real-time sensors, and will allow their use in areas and media not currently attainable by current systems.

Resin/adsorbent systems and real-time sensor systems can be modified into other specialized designs, however they may not be as adaptable to the platforms mentioned within this application.

Example XIII

Use of Multiple Ion Exchange Materials in a System

If multiple resins are used in the same sampler housing, the packets of different resins will be separated following use, for their respective, different leaching and chemical extraction processing. It may be more convenient to instead use multiple sampler housings, each with a different resin or resin blend to sample for multiple contaminates of concern. This way, the entire sampler housing with its contained resin may be put through the leaching and extraction processes, or, the resin packet of a single-type of resin may be removed from the housing and processed without the issues of separation of resins or resin packets.

Example XIV

Resin Packaging and Processing

The preferred packets that contain resin are hollow cylinders or a bendable/curvable pad/pillow, preferably with vertically-extending compartments or "sleeves". The packet/pad preferably is, or may bend/curve to be, a hollow generally cylindrical shape that is 1.5 to 2 inches in diameter with a nominal 0.25 inch wall thickness, for fitting into the annular space in the sampler of about the same dimensions. Multiple-compartment packets may include 2-10 sleeves, for example, with the preferred maximum being six vertical sleeves (for example, 6 vertical sleeves, with one positioned generally every 60 degrees around the 360 degree cylinder).

Many resins of current interest are granular, with the grain size varying from resin to resin, so that some resins may also be considered powders. Therefore, the term "granules" or "granular" in this disclosure may include granules, powders, and various particles. In the future, membranes and/or solid-profile adsorbents (for example, solid supports with the active materials on the support or made of the active materials) may be commercially available for the methods of the invention, and are included within the broad scope of the invention as a replacement for the granular resin/adsorbent. A membrane-based system may reduce the size of the unit, allowing for a greater flexibility in environmental media, offering miniscule sampling modules that can be glued, fastened, and/or otherwise fixed, for example by commercially-available means, onto equipment such as drill strings, spillways, and other fixed systems within effluents and media of concern. The benefit of the thin sleeve/cylinder packet of resin/adsorbent, containing currently-available granular or powder resins, is that it can be easily compressed and placed within a ¾ inch (nominal) diameter sample collection vial. By compressing the packet and resin contained therein, the end user can place the material within the vial, or optionally collapse the flexible packet into a flat shape, and then the chemicals may be leached and extracted from the resin using solvents and acids or other chemicals appropriate for the resin being utilized.

The benefit of the thin sleeve/cylinder packet of resin/adsorbent, containing currently-available granular or powder resins, is that it can be easily compressed and placed within a ¾ inch (nominal) diameter sample collection vial. By compressing the packet and resin contained therein, the end user can place the material within the vial, or optionally collapse the flexible packet into a flat shape, and then the chemicals may be leached and extracted from the resin using solvents and acids or other chemicals appropriate for the resin being utilized.

Example XV

Resin/Adsorbent Analysis

Figure 17:
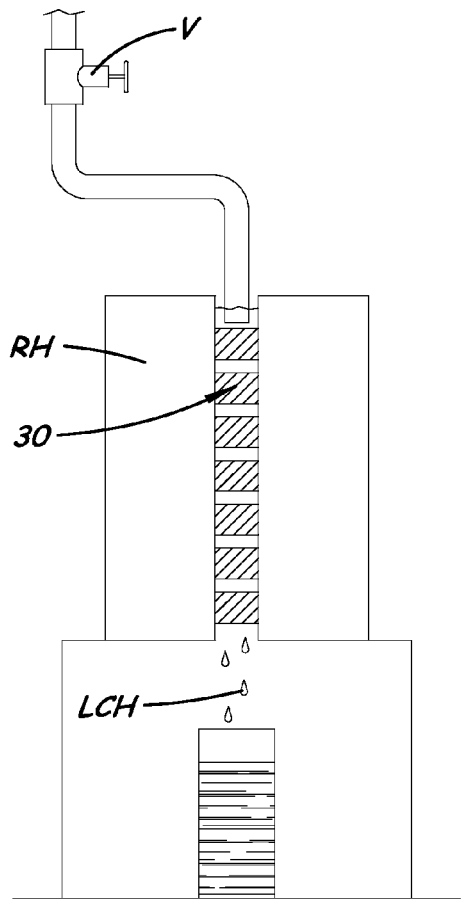
FIG. 17 portrays one embodiment of laboratory equipment and methods wherein a resin/adsorbent packet that has been removed from a sampler is installed in a holder for solvent extraction or other removal of chemicals/compounds that resulted from the sampler's exposure to the chemicals/compounds in the environment.
Figure 18:
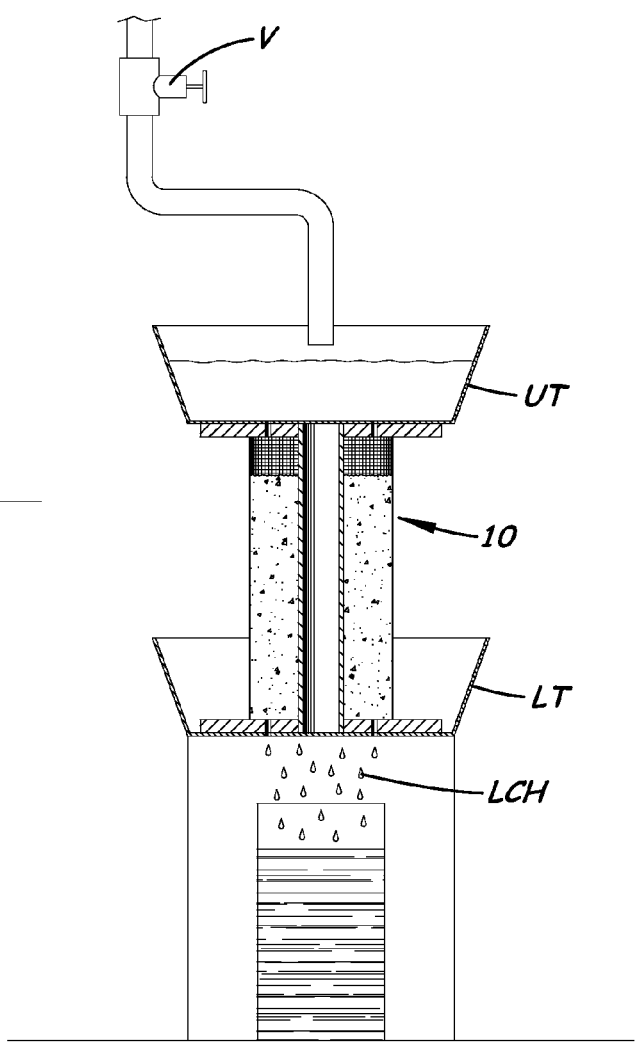
FIG. 18 is an alternative embodiment of laboratory equipment and methods wherein loose resin/adsorbent, removed from a sampler, is installed in a holder for solvent extraction or other removal of chemicals/compounds from the environment.

Referring to FIGS. 17 and 18, there are shown some, but the not the only, laboratory systems for analyzing packets of resin/adsorbents, or for analyzing the resin/adsorbent still contained in a sampler. In FIG. 17, a multiple-compartment packet of resin 30 is installed in a resin holder RH, so that a leaching solution may be dripped or otherwise flowed, in a controlled means such as by a valve V, down into the resin. The leachate LCH drips or flows into a vial or other container, for subsequent analysis of the contaminants/chemicals removed from the resin. In FIG. 18, a sampler 10 is set between a lower tray LT and an upper tray UT. Leaching solution flows in a controlled manner through holes in the upper tray, down into the sampler, preferably through the apertures (40 in FIGS. 1-3), for contact with the resin and removal of contaminants and chemicals captured by the resin. The leachate liquid flows out of the sampler again through apertures in the platform (24 in FIGS. 1-3), and into the lower tray. The leachate flows from holes in the lower tray to the vial/container.

Example, XVI

Using Multiple Sensors in a System, Spacers Between Sensors

Multiple sensor discs will be used in many embodiments of the invented sampling system. Where required by connectivity concerns, insulator materials such as plastic, composite or fiber-based materials will be used to segregate the materials to minimize interference. The spacers 52 shown in the figures are an example of such materials/insulators. Membrane sensors may become the preferred embodiment of the sensor discs in the future. As such, combining multiple arrays within a cylindrical remote sensing array would complement the platforms mentioned within this submittal; therefore, while multiple sensor disc are shown in the figures, a single sensor body comprising such an array or multiple membranes of sensor materials, could be used. Spacers or insulating material could be used internally in the single sensor body, for segregation efforts would be for the purpose of connectivity and minimizing signal interference.

Example XVII

Motorized Arm for the Sewer System

As discussed above for FIG. 13, a motorized retrieval system may be used to guide and improve the ease of placement and retrieval of the samplers. A battery-operated drill-type mechanism can be used (forward and reverse settings) to place and retrieve the systems from the sanitary/industrial sewer system. A top and bottom nut will be attached below and above the spacers that retain the ion-exchange resin samplers. A corkscrew rod (helix/worm gear) may be attached to the cabling system where it is desirable to continually place and retrieve samples for effluent sampling. A hand-held drill unit may reverse the nut assembly on the corkscrew rod to retrieve the samplers without binding, while the same is true for placement (by simply changing the direction of the drill). A bottom and top spacer may be fixed to the top and bottom of the cable allowing the operator to easily know when the sampler is at the desired placement position.

The advantages associated with a motorized device such as this may include: rapid deployment and re-deployment; supports long-term sampling stations; allows for easy replacement of samplers without removing the deployment fixture; can be adjusted to accommodate different depths or sampling locations; allows multiple samplers to be deployed at multiple depths; and/or used in residential sewer or discharge piping providing ready access to the desired sampling medium with minimal disruption of systems.

Example XVII

Retention Cage for Floating in a Pipe or Vessel

A retention cage is one option that allows a sampler cylinder(s) to float as the liquid level changes, so that the sampler always remains in contact with the medium being sampled. This concept is deployed in environments that constantly or frequently fluctuate, such as but not limited to, liquid levels in sewer or discharge pipes and/or vessels, tanks or basins. The retention cage concept is more clearly defined by the following two designs.

The sampler cylinder is placed in a fluctuating environment within a manufactured cage. The cage itself may be cylindrical in design, for example, with small circular cutouts integrated into the design which would allow liquid to easily flow through the cage. The retention cage is nominally 2 feet long for a sewer pipe, although it could be manufactured in shorter or longer lengths should the system see smaller or larger fluctuations in effluent flow conditions. A large tank or basin may need a much longer cage. The retention cage is fixed to a cable/rod at a position the captures the minimum and maximum flow conditions for a given system. The cage simply retains the cylinder/sampler and allows the resin system to float at the optimal level to capture organics or other chemicals of concern. The buoyancy and specific gravity of the sampler is designed to free float on the surface, for example, for the resin to contact the organic layer that may be floating on the surface of water.

Another retention concept is to manufacture the cylinder out of chemically resistant material (e.g. plastic/teflon) that allows the sampler to freely float between two widely-spaced locking washers that are attached to a cable or rod. The retrievable cable or rod system can be used with both fixed placement cylinders and this secondary retention device that allows the upper most sampler(s) to float on the top layer of the liquid. Fixed spacers are attached below the "low flow" point on the system with a top spacer affixed to correspond to the maximum flow height. The internal diameter of the cylinder passageway can be enlarged to provide clearance (reducing friction) and improving the free-floating characteristic necessary to allow the top organic sampler to remain on the surface of the liquid flow. Spacing of the fixed spacers allows the sampler to float on top of the effluent flow at all times allowing the system to be in contact with organic materials whether they be in low flow or high flow conditions.

General Comments:

Detection methods and apparatus have been developed, for assessing presence and buildup of contaminants and chemicals of concern. The methods and apparatus may include, for example: assessing long term buildup of chemicals; measuring miniscule amounts of materials not otherwise measured (considering as a function of the environment and environmental media surrounding the sampler such as high stream and sewer flows—capturing ions and cations as they pass through the resin); use of ion-exchange resins for environmental monitoring purposes; seepage from groundwater tables; providing a time release capability by providing a system that can demonstrate the effectiveness of treatment claims; an engineered system capable of remote sensing discs and wafers; a buoy system supported by GPS and telemetry; an engineered system supported by GPS and telemetry; and/or a single sampler capable of providing a resin cylinder that supports data collection for time release and phased detection studies with a need to integrate and compare the environmental data to real-time sensors that are part of an integral unit.

The sampler may contain a single ion-exchange resin bed/bag/sleeve, or multiple ion-exchange resin beds/bags/sleeves for the detection of multiple environmental elements of concern. The housing of the sampler may be manufactured out of multiple materials, for example, corrosion resistant elements such as stainless steel.

In certain embodiments, the sampler may be single one-piece unit where the ion exchange resin is placed in a non-removable housing (e.g. alleviating the need to handle potentially harmful materials such as analyzing resin for radioactive materials therefore reducing personnel exposure concerns. The sampler may be attached to a cable or other hardware allowing for precise placement within a watershed, sanitary sewer or in-stack monitoring (allowing for precise placement and ease of retrieval).

Use of some embodiments of the invented system may allow study and analysis for time release buildup for use in the following applications, for example: natural resource damage assessments including petroleum detection and crude oil degradation by-products; chemical and chemical agents of concern for Homeland Security; radiological detection and measurement; illegal drug manufacturing; cetection system for POTW/NPDES monitoring of hazardous wastes and other chemicals of concern; in-stack monitoring; down-wind monitoring; over-spray analysis; nutrient loading and analysis within watersheds; mine runoff and evaluations; sediment analysis including analysis of contaminant migration through the vadose zone; surface water runoff analysis; and/or water quality analysis including salt-water environments.

Integration of remote sensing discs may allow for real-time measurement of chemicals, environment conditions, and materials. The preferred discs are designed to be an integral part of the sampler system. Sensors can be a single unit such as a single disc or body with one or more sensing materials and electronics/transmission equipment, or may be multiple discs, sensors and/or membranes with said electronics/transmission equipment.

Integration and telemetry may be provided by a floating buoy system for aquatic environments that can be powered by solar cells. Telemetry and GPS interface may be used in remote environments. Embodiments of the invention may be integrated into land-based and other fixed samplers (e.g. sanitary sewer, stack monitoring).

The ion-exchange resin will be selected and tested to match the needs of the client and project and may include mixed ion-exchange resin beds for tracking of contaminants. The preferred sampler system is unique in that it allows packaging of multiple resins within a single cylindrical housing and allows the sampler to be placed within an environmental media (at preselected depths and locations) and/or on a tethered or fixed system. Tethered or fixed systems are unique since they allow the system to be placed in fixed locations such as those within municipal sewer systems that can be easily retrieved following the sampling campaign. The sampler is designed to offer unique options for today's difficult challenges within the environment.

Another unique feature with this sampler is the advantages it can offer to decision-makers such as those affected with the assessment of natural resource damage assessments. When coupled with remote sensing discs, the assessment team can gain access to real-time response data such as dissolved oxygen, pH, temperature, soil moisture and targeted specific remote sensing collection materials that when linked to real time telemetry and GPS system can offer the user the advantage of linking real time data with the collection of data related to time affected accumulation data associated with the ion-exchange cylinder.

The sensing discs are combined into a small engineered package and will either complement the collection of environmental data with the system and/or provide a scientific platform that allows the scientific community the tools which to evaluate environmental data collected by this system. Remote sensing materials and systems are easily adaptable into the smaller discs allowing the ability to offer a unique delivery tool and system for the environmental community.

Some embodiments of the invention may be described as an environmental monitoring system comprising: a sampler having a housing surrounding an interior space for receiving adsorbent that is adapted to adsorb at least one atom, ion or molecule from the environment in which the sampler is placed, the housing comprising a fluid-permeable outer screen and an inner stem, wherein said interior space is between said outer screen and inner stem; and a real-time sensor connected to the sampler for sensing physical parameters or chemicals in said environment; and a telemetry base comprising telemetry equipment provided a distance from the sampler and real-time sensor; wherein the real-time sensor is adapted to transmit data signals to said telemetry base for further transmission to a laboratory or control station, said data signals comprising data on said physical parameters or chemicals. The outer screen is preferably cylindrical and said stem is preferably cylindrical, with said interior space being an annular space, but the screen and stem may be other shapes. The system may further comprise multiple of said real-time sensors, each sensor being adapted to sense a different physical parameter or chemical or matter such as bacteria. The physical parameters or chemicals may be selected from the group consisting of temperature, dissolved oxygen, pH, clarity, bacteria, conductivity, organic compounds, and inorganic compounds, but may alternatively be selected from other parameters/chemicals. The housing may have a top and a bottom, a longitudinal axis from said top to said bottom, and the stem may have a passageway on said longitudinal axis, wherein the sampler is attached to an elongated supporting member that extends through the passageway. The top and bottom of the housing may be a top cap and bottom platform of various shapes, including but not limited to top and bottom plates. The system may further comprise a buoy for floating in water, wherein the elongated supporting member hangs from said buoy. The system may further comprise a weight attached to the elongated supporting member below the sampler. The real-time sensor may have an aperture and the elongated support member may extend through said aperture so that the real-time sensor is connected to said support member. The real-time sensor may rest on the top of the sampler, for example, by sliding down on top of the sampler by means of the sensor being slideably connected to the elongated member because the elongated member is received inside the aperture, for example with the elongated member being of smaller diameter than the aperture.

Certain embodiments of the environmental monitoring system may be described as comprising: a sampler having a generally cylindrical housing surrounding an interior space for receiving adsorbent that is adapted to adsorb at least one atom, ion or molecule from the environmental medium in which the sampler is placed, the housing having a top and a bottom and comprising a cylindrical fluid-permeable outer screen, an inner stem coaxial with the cylindrical outer screen, a cap at the top of the sampler and a platform at the bottom of the sampler, wherein said interior space is an annular space between said outer screen, inner stem, cap and platform; a support base; and an elongated member having a top end and a bottom end, the top end of the elongated member being attached to the support base, and the sampler being attached to the elongated member, so that the elongated member with attached sampler extends down from the support base to contact the environmental medium so that the adsorbent adsorbs said at least one atom, ion, or molecule from the environmental medium. The inner stem may have a passageway through the inner stem from the top to the bottom of the housing, and a plurality of said samplers may be attached to the elongated member with the elongated member extending through the passageway of the inner stem of each sampler. The elongated member may be selected from a group consisting of a cable, a bar, an arm, a chain, and a string, for example. The support base may comprise telemetry equipment, and the monitoring system further may comprise a real-time sensor connected to the elongated member at or near at least one of said samplers, wherein the real-time sensor is adapted to sense a physical parameter of the environmental medium at or near said at least one sampler and adapted to transmit data about said physical parameter wireless or by wire to the support base telemetry equipment. The support base may comprise telemetry equipment, and the monitoring system may further comprise a real-time sensor connected to the elongated member at or near at least one of said samplers, wherein the real-time sensor is adapted to sense a chemical in the environmental medium at or near said at least one sampler and adapted to transmit data about said chemical wireless or by wire to the support base telemetry equipment. The physical parameter may be selected from the group consisting of temperature, pH, clarity, and conductivity, for example. The chemical may be selected from the group consisting of dissolved oxygen, organic compounds, and inorganic compounds, for example. The real-time sensor may have a central axis and an aperture at the central axis, and the real-time sensor may be attached to the elongated member by the elongated member extending through the aperture. The support base may comprise telemetry equipment, and the monitoring system further may comprise a plurality of real-time sensors connected to the elongated member at or near at least one of said samplers, with each of the real-time sensors being adapted to sense a physical parameter of the environmental medium or a chemical in the environmental medium, at or near said at least one sampler and adapted to transmit data about said physical parameter and chemical wirelessly or by wire to the support base telemetry equipment.

Certain embodiments of the invention may comprise, consist essentially of, or consist of, a generally cylindrical housing having a top cap and a bottom platform, a cylindrical fluid-permeable outer screen extending between the top cap and the bottom platform, an inner stem coaxial with and inside the cylindrical outer screen, and an annular space between said outer screen, inner stem, top cap and bottom platform; wherein adsorbent is contained in the annular space (either loose and/or in a packet container made mainly or entirely of fluid-permeable fabric(s)/material(s)) for adsorbing at least one atom, ion, or molecule from an environmental medium around the sampler; and the inner stem has a passageway extending through the sampler for being received on an elongated support member for installing the sampler in the environmental medium. The inner stem may be fluid-permeable or fluid-impermeable or have portions of each. The adsorbent may be in one or multiple compartments of a packet, made of fluid-permeable fabric(s)/material(s), that is installed into the annular space, for example, a packet having multiple parallel compartments extending from the top to the bottom of the packet so that the packets extend axially in the annular space.

Although this invention has been described above with reference to particular means, materials, and embodiments, it is to be understood that the invention is not limited to these disclosed particulars, but extends instead to all equivalents within the broad scope of the following claims.

The invention claimed is:

1. A sampler for monitoring an environmental medium comprising fluid, the sampler comprising:
   a generally cylindrical housing having an axial dimension and a radial dimension, an outer axial side-wall, a cap and a platform at opposite ends of said side-wall, an inner stem coaxial with and inside the side-wall, and an annular space between said side-wall, inner stem, cap and platform;
   an adsorbent contained in the annular space for adsorbing at least one atom, ion, or molecule from an environmental medium around the sampler; and
   the inner stem having a passageway extending through the sampler for being received on an elongated support member for installing the sampler in the environmental medium with the environmental medium contacting the side-wall;
   wherein the side-wall is entirely or substantially fluid-permeable so that the sampler is adapted for fluid from the environmental medium to enter the sampler through the side-wall to contact said adsorbent inside the annular space.

2. A sampler as in claim 1, wherein the inner stem is fluid-permeable.

3. A sampler as in claim 1, wherein the inner stem is fluid-impermeable.

4. A sampler as in claim 1, wherein the adsorbent in the annular space is inside multiple compartments of a packet made of fluid-permeable fabric.

5. A sampler as in claim 1, wherein the adsorbent is an ion-exchange resin adapted to collect from its environment a contaminant selected from the group consisting of: herbicides, pesticide, heavy metals, organic compounds, and radionuclides.

6. A sampler as in claim 4, wherein the adsorbent is an ion-exchange resin adapted to collect from its environment a contaminant selected from the group consisting of: herbicides, pesticide, heavy metals, organic compounds, and radionuclides.

7. A sampler as in claim 1, further comprising apertures through each of the cap and the platform, for allowing solvent or other fluid to enter the annular space through said apertures in the cap and leave the annular space through said apertures in the platform.

8. A sampler as in claim 7, wherein said apertures through the cap are provided in a circular pattern.

9. A sampler as in claim 7, wherein said apertures through the platform are provided in a circular pattern.

10. A sampler as in claim 1, wherein the cap is generally planar and extends radially out past the outer axial side-wall.

11. A sampler as in claim 1, wherein the platform is generally planar and extends radially out past the outer axial side-wall.

12. A sampler as in claim 1, wherein a rigid elongated member is received through the passageway, and said rigid elongated member comprises a screw-style lower end below the sampler adapted to be screwed into the ground.

13. A sampler as in claim 1, wherein said outer axial side-wall is the outermost extremity of the housing between the cap and the platform.

* * * * *